(12) United States Patent
Imamura et al.

(10) Patent No.: US 6,190,773 B1
(45) Date of Patent: Feb. 20, 2001

(54) SELF-WATER DISPERSIBLE PARTICLE MADE OF BIODEGRADABLE POLYESTER AND PROCESS FOR THE PREPARATION THEREOF

(75) Inventors: Shoji Imamura, Sakura; Yasuyuki Watanabe, Chiba; Kazuaki Tsukuda; Takashi Hirokawa, both of Sakura; Nagao Ariga, Abiko, all of (JP)

(73) Assignee: Dainippon Ink and Chemicals, Inc., Tokyo (JP)

( * ) Notice: Under 35 U.S.C. 154(b), the term of this patent shall be extended for 0 days.

(21) Appl. No.: 09/296,132

(22) Filed: Apr. 22, 1999

(30) Foreign Application Priority Data

Apr. 23, 1998 (JP) ................................................. 10-113343
Mar. 25, 1999 (JP) ................................................. 11-081359

(51) Int. Cl.[7] ............................ B32B 15/02; C08G 63/06
(52) U.S. Cl. ........................... 428/402; 528/354; 528/361; 524/604
(58) Field of Search ..................................... 528/354, 361; 524/604; 428/402

(56) References Cited

U.S. PATENT DOCUMENTS 5,855,915 * 1/1999 Pinkus ................................... 424/486

* cited by examiner

Primary Examiner—Samuel A. Acquah
(74) Attorney, Agent, or Firm—Armstrong, Westerman, Hattori, McLeland & Naughton

(57) ABSTRACT

A self-water dispersible particle made of a biodegradable polyester and a process for the preparation of an aqueous dispersion of self-water dispersible particles made of a biodegradable polyester containing a hydrophobic core material, which comprises reacting a biodegradable polyester containing hydroxyl group with a polyvalent carboxylic acid or anhydride or chloride thereof, dissolving or dispersing the biodegradable polyester having acid groups thus obtained and a hydrophobic core material in an organic solvent, adding a base to the solution with stirring to neutralize to form the salt of the biodegradable polyester, and then adding water to the solution or dispersion to undergo phase inversion emulsification are disclosed. According to the present invention, a self-water dispersible particle made of a biodegradable polyester having varied average particle diameters of the order of nanometer free of urethane bond and excellent in biodegradability, an aqueous dispersion thereof, a self-water dispersible particle made of a biodegradable polyester comprising a hydrophobic core material encapsulated therein excellent in gradual releasability such as pesticide, and a process for the simple preparation of these products without using any auxiliary stabilizing material such as emulsifying agent or any high speed agitator can be provided.

11 Claims, 3 Drawing Sheets

10 μm

10 μm

SELF-WATER DISPERSIBLE PARTICLE MADE OF BIODEGRADABLE POLYESTER AND PROCESS FOR THE PREPARATION THEREOF

FIELD OF THE INVENTION

The present invention relates to a self-water dispersible particle made of a biodegradable polyester and a process for the preparation thereof. More particularly, the present invention relates to a self-water dispersible particle made of an extremely small biodegradable polyester having a size of the order of nanometer which can comprise various hydrophobic core materials encapsulated therein and a process for the preparation thereof.

The self-water dispersible particle made of a biodegradable polyester according to the present invention can find wide application such as various preparations (e.g., pesticide, pharmaceutical preparations, fertilizer), particularly gradually-releasable preparations, coating agents for fishing net, layer farming net, etc., coating for the bottom of ship, gradually-releasable repellent against small animals to be scattered over sandbox in park or the like, coating, ink, toner, adhesive, lamination for paper, foaming resin material, fire extinguishing agent, cosmetic material, construction material, etc.

BACKGROUND OF THE INVENTION

In an attempt to render pharmaceutical preparations or pesticides gradually releasable, extensive studies have been made of particulate or microcapsuled resin comprising a polyester, particularly a biodegradable polyester. For example, JP-A-6-72863 (The term "JP-A" as used herein means an "unexamined published Japanese patent application"), JP-A-8-157389, and JP-A-9-208494 disclose a technique concerning gradually-releasable pharmaceutical preparations comprising a lactic acid-based polymer as an aliphatic polyester.

These microcapsulization processes include a process which comprises adding a solution or dispersion obtained by dissolving a lactic acid-based polymer which doesn't have hydrophilic groups sufficiently in an organic solvent and dissolving or dispersing medicines in the solution dropwise to an aqueous solution containing a surface active agent, stirring the mixture to form an oil-in-water type emulsion or adding the solution or dispersion dropwise to an oil immiscible with the solution or dispersion, stirring the mixture to form an oil-in-oil type emulsion, and then evaporate the solvent away from the emulsion to solidify the microcapsule (submerged drying process) and a process which comprises stirring the foregoing solution or dispersion while a solvent miscible with the solution or dispersion but incapable of dissolving the polymer (so-called poor solvent) is being added thereto so that the polymer undergoes phase separation to prepare a microcapsule (coacervation process).

The microcapsule obtained by these preparation processes comprises a constituent polymer which doesn't have hydrophilic groups sufficiently as defined herein and thus doesn't exhibit so-called self-water dispersibility. Thus, the addition of an auxiliary such as surface active agent during the preparation of microcapsule is indispensable. High speed agitation is required as well. Further, it is difficult to prepare extremely small particles having a size of the order of nanometer.

JP-A-6-313024 discloses a technique concerning an aqueous polyurethane resin prepared by neutralizing with a base a lactone-based polyurethane resin having a carboxylic acid comprising a lactone-based polyester polyol obtained by ring opening polymerization of lactone in the presence of a dihydroxycaboxylic acid as an initiator, a diisocyanate and a chain extender.

The above proposed method can provide a self-water dispersible particle as well. However, this method doesn't allow two or more carboxyl groups to be introduced into molecular chain unless diisocyanates, which are undesirable for living body or environment, are used. Further, in order to reduce the particle size of the particulate material to an extent such that it is rendered self-water dispersible, it is necessary to raise the acid value in the polymer. To this end, the particulate material needs to contain a large amount of urethane bond. Accordingly, the desired physical properties of polyester can be hardly maintained, causing deterioration of biodegradability.

Many methods for the preparation of capsulized pesticides obtained by microcapsulizing pesticide activator components have been known. For example, JP-A-6-362, JP-A-6-238159, JP-A-7-165505, JP-A-8-53306, JP-A-9-249505, and JP-A-9-57091 disclose a method for the preparation of capsulized pesticides by interfacial polymerization method using polyurea or polyurethane as a wall material.

Further, JP-A-5-155714 discloses a method for the preparation of capsulized pesticides involving the copolymerization of an unsaturated polyester resin with a vinyl monomer in the presence of a hardening initiator. JP-A-5-70663 discloses a method for the preparation of capsulized pesticides comprising acryl copolymer. All these methods comprise emulsion-dispersing a resin and a chemical in water, and then allowing the dispersion to undergo polymerization at particle interface or inside the particles to prepare a capsulized pesticide. An emulsifying agent is essential to disperse these components in water.

It has thus been desired to develop a particulate self-water dispersible biodegradable material having an average particle diameter as small as nanometer free of urethane bond and excellent in biodegradability, and a process for the preparation of a particulate self-water dispersible biodegradable material without using any isocyanate which is undesirable for living body or environment or emulsifying agent and any high rotary speed agitator.

SUMMARY OF THE INVENTION

It is therefore an object of the present invention to provide a self-water dispersible particle made of a biodegradable polyester having varied average particle diameters of the order of nanometer, free of urethane bond and excellent in biodegradability, an aqueous dispersion thereof, a self-water dispersible particle made of a biodegradable polyester comprising a hydrophobic core material encapsulated therein excellent in gradual releasability such as pesticide, and a process for the simple preparation of these products without using any auxiliary stabilizing material such as emulsifying agent or any high speed agitator.

The inventors made extensive studies. As a result, a process for the simple preparation of a self-water dispersible particle made of a biodegradable polyester, an aqueous dispersion thereof, a self-water dispersible particle comprising a hydrophobic core material encapsulated therein excellent in gradual releasability such as pesticide without using any auxiliary stabilizing material such as emulsifying agent has been found which comprises reacting a biodegradable polyester having hydroxyl groups with a polyvalent carboxylic acid or anhydride or chloride thereof to obtain a biodegradable polyester having acid groups, adding a base to the biodegradable polyester in an organic solvent with stirring to neutralize to form the salt of the biodegradable polyester, and then adding water to the material so that it undergoes phase inversion emulsification. The present invention has thus been worked out.

The present invention has the following constitutions:

(1) A self-water dispersible particle made of a biodegradable polyester.

(2) The self-water dispersible particle made of a biodegradable polyester according to Clause (1), wherein said biodegradable polyester contains carboxyl groups and/or salt thereof.

(3) The self-water dispersible particle made of a biodegradable polyester according to Clause (2), wherein said biodegradable polyester has an acid value of from 4 to 200 KOHmg/g.

(4) The self-water dispersible particle made of a biodegradable polyester according to Clause (3), wherein said biodegradable polyester contains dimethylolpropionic acid residues.

(5) The self-water dispersible particle made of a biodegradable polyester according to any one of Clauses (1) to (4), wherein said biodegradable polyester is a lactic acid-based polymer.

(6) The self-water dispersible particle made of a biodegradable polyester according to any one of Clauses (1) to (4), wherein said biodegradable polyester is an aliphatic polyester.

(7) The self-water dispersible particle made of a biodegradable polyester according to any one of Clauses (1) to (4), wherein said biodegradable polyester is a lactone-based polymer.

(8) The self-water dispersible particle made of a biodegradable polyester according to Clause (5), wherein said lactic acid-based polymer is a polylactic acid.

(9) The self-water dispersible particle made of a biodegradable polyester according to Clause (5), wherein said lactic acid-based polymer is a lactic acid-based polyester copolymer comprising a lactic acid unit and a polyester unit.

(10) The self-water dispersible particle made of a biodegradable polyester according to any one of Clauses (1) to (9), comprising a hydrophobic core material encapsulated therein.

(11) The self-water dispersible particle made of a biodegradable polyester according to Clause (10), wherein said hydrophobic core material is an effective component of pesticide.

(12) A process for the preparation of an aqueous dispersion of self-water dispersible particles made of a biodegradable polyester according to any one of Clauses (1) to (9), comprising:

(i) a step of reacting a biodegradable polyester having hydroxyl groups with a polyvalent carboxylic acid or anhydride or chloride thereof to obtain a biodegradable polyester having acid groups; and (ii) a step of dissolving the biodegradable polyester having acid groups obtained in the step (i) in an organic solvent, adding a base to the solution with stirring to neutralize to form the salt of the biodegradable polyester having acid groups, and then adding water to the resulting solution or dispersion to undergo phase inversion emulsification.

(13) A process for the preparation of an aqueous dispersion of self-water dispersible particles made of a biodegradable polyester having a hydrophobic core material encapsulated therein according to Clause (10), comprising:

(i) a step of reacting a biodegradable polyester having hydroxyl groups with a polyvalent carboxylic acid or anhydride or chloride thereof to obtain a biodegradable polyester having acid groups; and (ii) a step of dissolving or dispersing the biodegradable polyester having acid groups obtained in the step (i) and a hydrophobic core material in an organic solvent, adding a base to the solution or dispersion with stirring to neutralize to form the salt of the biodegradable polyester having acid groups, and then adding water to the resulting solution or dispersion to undergo phase inversion emulsification.

(14) The process for the preparation of an aqueous dispersion of self-water dispersible particles according to Clause (13), wherein said hydrophobic core material is an effective component of pesticide.

(15) The process for the preparation of an aqueous dispersion of self-water dispersible particles made of a biodegradable polyester according to any one of Clauses (12) to (14), wherein said biodegradable polyester having acid groups has an acid value of from 4 to 200 KOHmg/g.

(16) The process for the preparation of an aqueous dispersion of self-water dispersible particles made of a biodegradable polyester according to Clause (15), wherein said biodegradable polyester having acid groups contains dimethylolpropionic acid residues.

(17) The process for the preparation of an aqueous dispersion of self-water dispersible particles made of a biodegradable polyester according to any one of Clauses (12) to (16), wherein said biodegradable polyester having hydroxyl groups is a lactic acid-based polymer.

(18) The process for the preparation of an aqueous dispersion of self-water dispersible particles made of a biodegradable polyester according to any one of Clauses (12) to (16), wherein said biodegradable polyester having hydroxyl groups is an aliphatic polyester.

(19) The process for the preparation of an aqueous dispersion of self-water dispersible particles made of a biodegradable polyester according to any one of Clause (12) to (16), wherein said biodegradable polyester having hydroxyl groups is a lactone-based polymer.

(20) The process for the preparation of an aqueous dispersion of self-water dispersible particles made of a biodegradable polyester according to Clause (17), wherein said lactic acid-based polymer is a polylactic acid.

(21) The process for the preparation of an aqueous dispersion of self-water dispersible particles made of a biodegradable polyester according to Clause (17), wherein said lactic acid-based polymer is a lactic acid-based polyester copolymer comprising a lactic acid unit and a polyester unit.

(22) A process for the preparation of an aqueous dispersion of self-water dispersible particles made of a biodegradable polyester, which comprises separating particles from an aqueous dispersion obtained by the preparation method according to any one of Clauses (12) to (21).

DETAILED DESCRIPTION OF THE INVENTION

Figure 1:
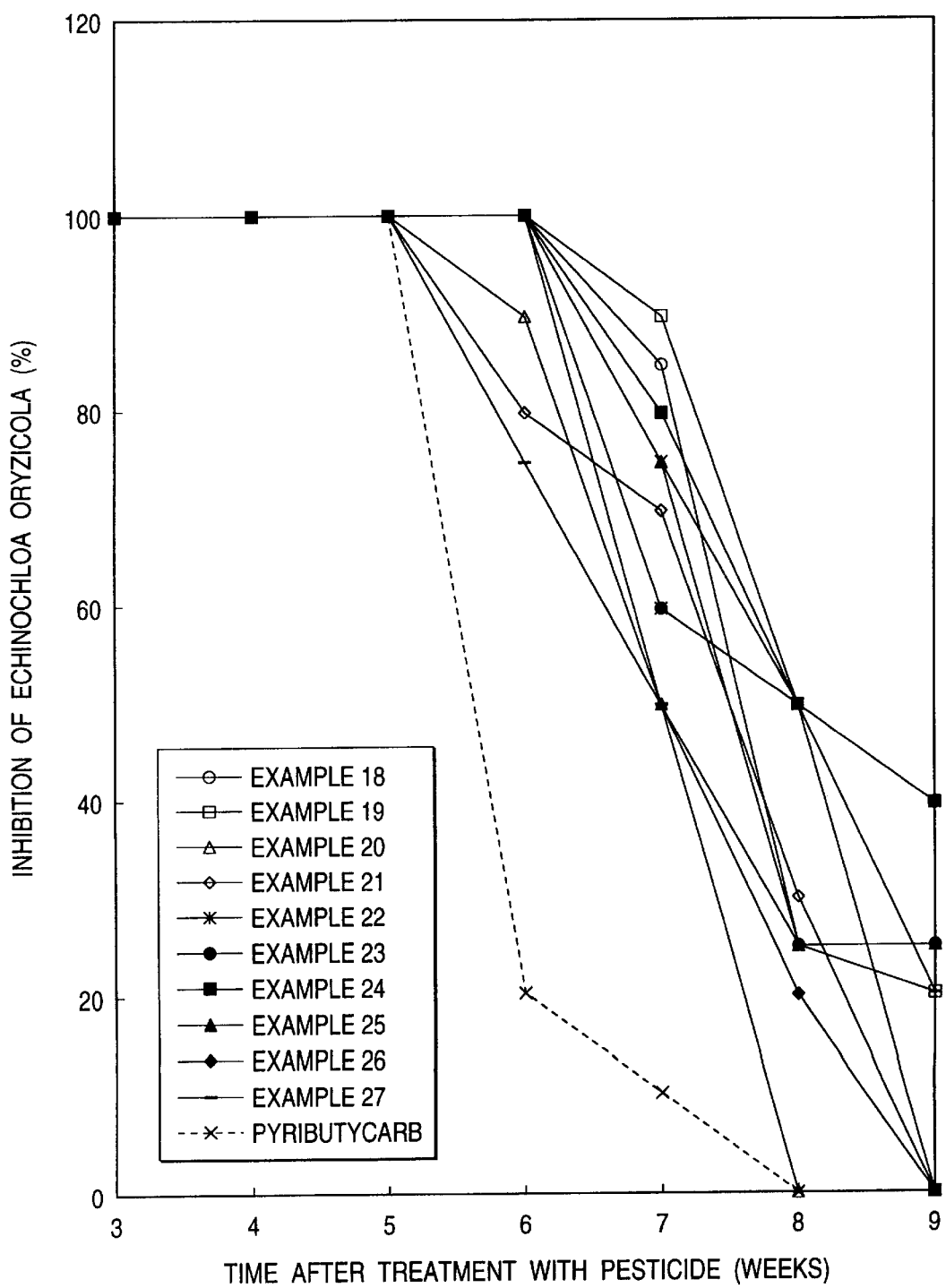
FIG. 1 is a graph illustrating the relationship between the elapsed time after treatment with pesticide and the percent inhibition of *Echinochloa oryzicola*.

The present invention will be further described hereinafter.

As the biodegradable polyester to be used herein there may be used any polymer generally called biodegradable polyester having hydroxyl groups. For example, a lactic acid-based polymer may be used.

The term "lactic acid-based polymer" as used herein is meant to indicate a polymer containing a lactic acid unit (residue). Specific examples of such a polymer include polylactic acid comprising the repetition of lactic acid residues, lactic acid-based polyester copolymer comprising a glycolic acid unit and a lactic acid unit, lactic acid-based polyester copolymer comprising a lactic acid unit and a polyester unit, and lactic acid-based polyether polyester copolymer comprising a lactic acid unit and a polyether polyol unit.

Further examples of such a polymer include polyglycolic acid, aliphatic polyester such as Bionolle (produced by SHOWA HIGHPOLYMER CO., LTD.), lactone-based polyester such as poly-ε-caprolactone, and polyhydroxy butyrate-based polyester such as Biopol (produced by ICI Inc.). Employable herein among these biodegradable polyesters are those having a polymer comprising hydroxyl group incorporated therein.

These copolymers of glycolic acid with lactic acid, polylactic acids, lactic acid-based polyesters comprising a lactic acid unit and a polyester unit, lactic acid-based polyether esters comprising a lactic acid unit and a polyether polyol unit, aliphatic polyesters such as Bionolle (produced by SHOWA HIGHPOLYMER CO., LTD.), and lactone-based polyesters such as poly-ε-caprolactone are desirable because they can have controlled molecular weight. From the standpoint of adaptability to living body, lactic acid-based polymers, particularly polylactic acid and lactic acid-based polyester copolymer comprising a lactic acid unit and a polyester unit, are desirable.

The term "self-water dispersibility" as used herein is meant to indicate capability of being dispersed stably in water in the absence of an emulsifying agent or emulsifying aid such as water-soluble protective colloid resin as an essential component. In order to render the foregoing biodegradable polyester self-water dispersible, an anionically functional group (e.g., carboxyl group, sulfonic group) or cationically functional group (e.g., amino group) may be incorporated in the biodegradable polyester. Carboxyl group is particularly desirable from the standpoint of ease of incorporation.

The term "acid value" as used herein is meant to indicate the amount (mg) of KOH required to neutralize the acid group present in 1 g of the resin (unit: KOHmg/g). The theoretical equation is represented by the following equation (1)

$$\text{Acid value (KOHmg/g)} = (1 \text{ g} \times n)/\text{Mn} \times 56.1 \times 1{,}000 \quad (1)$$

wherein n represents the number of carboxylic acid groups per mol of self-water dispersible polyester; and Mn represents the number-average molecular weight of self-water dispersible polyester.

The process for the preparation of a biodegradable polyester having an acid to be used herein, i.e., process for the incorporation of a carboxylic acid group in a biodegradable polyester having hydroxyl groups will be described hereinafter.

The aliphatic polyester (starting material) to be used as a base can be prepared by any ordinary known conventional polycondensation reaction. In some detail, an aliphatic polyvalent carboxylic acid and a polyhydric alcohol as starting materials are allowed to undergo dehydro-polycondensation in the presence or absence of solvent and in the presence or absence of catalyst.

The polyvalent carboxylic acid may be partially subjected to dealcoholation polycondensation using an alkylesterification product thereof. In order to increase the molecular weight of the aliphatic polyester, deglycolation reaction may be effected under reduced pressure. Alternatively, the polyvalent carboxylic acid can be obtained by ring-opening polymerization of, e.g., succinic anhydride and ethylene oxide.

The aliphatic polyvalent carboxylic acid employable herein is not particularly limited. Specific examples of the aliphatic polyvalent carboxylic acid include aliphatic dicarboxylic acid such as succinic acid, succinic anhydride, adipic acid, azelaic acid, sebasic acid, brasylic acid, cyclohexane dicarboxylic acid and alkylester thereof. These polyvalent carboxylic acids may be used singly or in combination.

Examples of the polyhydric alcohol component employable herein include diol such as ethylene glycol, triol such as glycerin, tetraol such as pentaerythritol, and polyether polyol such as polyethylene glycol.

Particularly preferred among these polyhydric alcohol components is $C_{2\text{-}10}$ diol. Specific examples of the $C_{2\text{-}10}$ diol employable herein include ethylene glycol, propylene glycol, butylene glycol, pentanediol, hexamethylene glycol, octanediol, neopentyl glycol, cyclohexanediol, cyclohexane dimethanol, diethylene glycol, and hydrogenated bisphenol A.

Further, cyclic compounds such as ethylene oxide and propylene oxide may be used. These polyols may be used singly or in combination.

In order to incorporate carboxyl groups in the aliphatic polyester having hydroxyl groups, a polyvalent carboxylic acid or anhydride or chloride thereof is added to the aliphatic polyester so that the hydroxyl group in the aliphatic polyester is esterified into carboxyl group.

Specific examples of the foregoing preparation process include a process which comprises charging a polyester having hydroxyl groups and a polyvalent carboxylic acid or anhydride thereof into a reactor where they are reacted under reduced pressure, a process which comprises reacting a polyester having hydroxyl groups with a polyvalent carboxylic acid in a solvent under heating, and then removing the water thus produced by azeotropy with the solvent, a process which comprises adding a polyvalent carboxylic anhydride to the hydroxyl group in a polyester at a high temperature, and dehydrochloration reaction using an acid chloride. Any of these processes may be used. The reaction temperature is normally from 70° C. to 220° C., preferably from 100° C. to 200° C., more preferably from 100° C. to 180° C., to inhibit ester exchange reaction.

The foregoing reaction may be effected in the presence of a catalyst. As such a catalyst there may be used any of catalysts known as esterification catalyst. Examples of such an esterification catalyst include strong acid such as sulfuric acid and p-toluenesulfonic acid and at least one organic or inorganic compound of metal selected from the group consisting of Li, Na, K, Zn, Co, Mn, Ti, Sn, Fe, Al and Mg. In particular, alkoxide, organic acid salt and oxide of metals are desirable. As the catalyst for use in the addition of a carboxylic anhydride to the hydroxyl group in the polyester there may be used the foregoing catalyst as well as amine such as imidazole or pyridine.

Among these catalysts, titanium tetraisopropoxide, titanium tetrabutoxide, titanium oxyacetylacetonate, and ferric (III) acetylacetonate allow rapid reaction and thus are desirable. The amount of such a catalyst to be used is normally from 1 to 1,000 ppm, preferably from 10 to 200 ppm taking into account the polymerization rate and the color of the polymer thus obtained.

The polyvalent carboxylic acid or anhydride or chloride thereof to be used in the carboxylation of the hydroxyl group in the polyester is not specifically limited and may be any known conventional compound. Specific examples of such a compound include succinic acid, succinic anhydride, adipic acid, sebasic acid, terephthalic acid, phthalic anhydride, trimellitic acid, trimellitic anhydride, pyromellitic acid, pyromellitic anhydride, tetrahydrofuran tetracarboxylic acid, tetrahydrofuran tetracarboxylic anhydride, dichloride succinate, dichloride adipate, and dichloride sebacate. Particularly preferred among these compounds are trimellitic acid, trimellitic anhydride, pyromellitic acid, pyromellitic anhydride, and tetrahydrofuran tetracarboxylic anhydride, which can raise the acid value of the biodegradable polyester.

The amount of the polyvalent carboxylic acid or anhydride or chloride thereof to be used in the carboxylation of hydroxyl group is from 0.1 to 2 mols per mol of the hydroxyl group contained in the polyester. In order to reduce the amount of unreacted carboxylic acid as much as possible, the amount of the polyvalent carboxylic acid or anhydride or chloride thereof to be used in the carboxylation of hydroxyl group is from 0.1 to 1.5 mols, preferably from 0.5 to 1.3 mols per mol of the hydroxyl group contained in the polyester.

As the process for the addition of the carboxylic acid group to the aliphatic polyester there may be used a process which comprises adjusting the charged amount of aliphatic polyvalent carboxylic acid and polyol during the polycondensation reaction such that the eventually obtained polyester terminal can become a carboxylic acid group. This can be normally accomplished by charging the aliphatic polyvalent carboxylic acid in a molar amount exceeding that of the polyhydric alcohol.

Any one of polyvalent carboxylic acids having acid groups having a valence of 3 or more such as trimellitic acid, trimellitic anhydride, pyromellitic acid and pyromellitic anhydride may be further charged into the aliphatic polyester in a small amount to form a star-shaped polymer so that the number of carboxylic acid groups per mol of polymer is increased.

Next, the polylactic acid, the copolymer comprising a glycolic acid unit and a lactic acid unit and the polyglycolic acid will be further described hereinafter. The preparation of a polylactic acid, a copolymer comprising a glycolic acid unit and a lactic acid unit or a polyglycolic acid from lactic acid and glycolic acid as starting materials can be accomplished by an ordinary known conventional polycondensation reaction. In some detail, dehydropolycondensation is effected in the presence or absence of solvent and in the presence or absence of catalyst. Of course, this reaction may be effected under reduced pressure.

The preparation of a polylactic acid, a copolymer comprising a glycolic acid unit and a lactic acid unit or a polyglycolic acid from a lactide, which is a cyclic dimer of lactic acid, and glycolide, which is a cyclic dimer of glycolic acid, can be accomplished by ring-opening polymerization in the presence of a ring-opening polymerization catalyst.

As the catalyst to be used herein there may be used any compound generally known as esterification catalyst or ring-opening polymerization catalyst. Examples of the catalyst employable herein include alkoxide, acetate, oxide and chloride of Sn, Ti, Zr, Zn, Ge, Co, Fe, Al, Mn, etc.

Preferred among these catalysts are tin octylate, dibutyltin dilaurate, tetraisopropyl titanate, tetrabutoxy titanium, titanium oxyacetylacetonate, ferric (III) acetylacetonate, ferric (III) ethoxide, aluminum isopropoxide, and aluminum acetylacetonate, which allow rapid reaction.

Examples of the lactide to be used as starting material include L-lactide made of two L-lactic acid molecules, D-lactide made of two D-lactic acid molecules, and meso-lactide made of L-lactic acid and D-lactic acid. A copolymer comprising L-lactide or D-lactide alone undergoes crystallization to exhibit a high melting point. The lactic acid-based polymer of the present invention comprises the three kinds of lactides in combination to realize desirable resin characteristics depending on the purpose. In the present invention, L-lactide is preferably incorporated in the lactide in an amount of not less than 75% based on the total amount of the lactide to realize better thermal physical properties. In order to realize even better thermal physical properties, L-lactide is preferably incorporated in the lactide in an amount of not less than 90% based on the total amount of the lactide.

The lactic acid-based polyester can be obtained by the polycondensation of lactic acid, a polyvalent carboxylic acid and a polyhydric alcohol, the polycondensation of lactic acid and polyester, or the copolymerization of lactide with a polyester. In particular, a lactide and a polyester can undergo rapid copolymerization reaction in the presence of a ring-opening polymerization catalyst, making it easy to control the molecular weight of the lactic acid-based polyester. Further, the resulting lactic acid-based polyester exhibits excellent physical properties. Thus, this process is advantageous. This polymerization may be effected in the presence of a catalyst. In particular, the copolymerization of a lactide with a polyester is preferably effected in the presence of a catalyst.

As such a catalyst there may be normally used an esterification catalyst or ring-opening polymerization catalyst as previously mentioned. Specific examples of such a catalyst include alkoxide, acetate, oxide and chloride of Sn, Ti, Zn, Ge, Co, Fe, Al, Mn, etc. Preferred among these catalysts are tin octylate, dibutyltin dilaurate, tetraisopropyl titanate, tetrabutoxy titanium, titanium oxyacetylacetonate, ferric (III) acetylacetonate, ferric (III) ethoxide, aluminum isopropoxide, and aluminum acetylacetonate, which allow rapid reaction.

As the starting materials to be used herein there may be used those described above with reference to dicarboxylic acid, polyhydric alcohol and lactide. The polyester employable herein is not specifically limited. Examples of the polyester to be used herein include aromatic polyester, aromatic aliphatic polyester, and aliphatic polyester. Further examples of the polyester to be used herein include lactone-based polyester such as poly-ϵ-caprolactone, and polyhydroxy butyrate-based polyester. Taking into account the biodegradability, however, aliphatic polyester, particularly the foregoing aliphatic polyester, lactone-based polyester such as poly-ϵ-caprolactone, and polyhydroxy butyrate-based polyester are desirable.

The lactic acid-based polyether polyester can be obtained by the polycondensation of lactic acid and a polyether polyol or the copolymerization of a lactide with a polyether polyol. In particular, a lactide and a polyether polyol can undergo rapid copolymerization reaction in the presence of a ring-opening polymerization catalyst, making it easy to control the molecular weight of the biodegradable polyester.

As the lactide to be used as a starting material there may be used one described above. The polyether polyol to be used herein is not specifically limited so far as it is a polymer generally called polyether polyol. For example, a diol type polyether polyol, which is terminated by hydroxyl group at both ends, or a triol or higher type polyether polyol, which is terminated by three or more hydroxyl groups, may be used without limitation. Specific examples of these polyether polyols include polyethylene glycol, polypropylene glycol, copolymer of ethylene oxide with propylene oxide, and polytetramethylene glycol.

The process for the preparation of a lactic acid-based polymer from a lactide will be further described hereinafter.

The ring-opening polymerization of a lactide or copolymerization of a lactide with a polyester or polyether polyol to a lactic acid-based copolymer is accomplished by a process which comprises heating the mixture so that it is molten, diluting the reactive materials with a solvent so that they are mixed, and then adding a polymerization catalyst to the mixture. The polymerization temperature is preferably from not lower than 100° C., which is the melting point of a lactide, to not higher than 220° C. from the standpoint of polymerization equilibrium. Within this polymerization temperature range, the coloring of the lactic acid-based polymer accompanying the decomposition reaction can be prevented. More preferably, the polymerization temperature is from 130° C. to 200° C.

In order to prevent the decomposition and coloring of the lactide, all the reactions are preferably effected in an atmosphere of dried inert gas, particularly nitrogen or argon gas, or bubbling inert gas. At the same time, the polyester or polyether polyol to be used as a starting material is preferably subjected to drying under reduced pressure so that it is freed of water content. Further, an oxidation inhibitor such as phosphite compound and phenol compound may be used.

A lactide can be dissolved in a solvent and thus can be polymerized in the presence of a solvent. Specific examples of the solvent employable herein include benzene, toluene, ethylbenzene, xylene, cyclohexanone, methyl ethyl ketone, and isopropyl ether. Such a solvent is preferably dried to remove water content therefrom, making it possible to suppress the unevenness of the molecular weight of the lactic acid-based polymer thus obtained.

The process for the incorporation of a carboxylic acid group in a lactic acid-based polymer or polyglycolic acid will be further described hereinafter. In the polycondensation reaction of a glycolic acid or lactic acid, a small amount of a polyvalent carboxylic acid may be added in the initial or final stage of the polymerization to increase the number of carboxylic acid groups at the end of the eventually obtained polyester. Examples of the polyvalent carboxylic acid employable herein include dicarboxylic acid such as succinic acid, adipic acid and sebasic acid, and polyvalent carboxylic acid such as trimellitic acid, trimellitic anhydride, pyromellitic acid and pyromellitic anhydride.

Alternatively, a carboxylic acid group may be introduced into the hydroxyl group in the lactic acid-based polymer or polyglycolic acid thus obtained. In some detail, a polyvalent carboxylic acid or anhydride or chloride thereof is added to esterify the hydroxyl group (mostly terminal hydroxyl group) in the lactic acid-based polymer to carboxyl group. This process can be effected in the same manner as described with reference to aliphatic polyester.

In order to further enhance the acid value of the glicolide, polyglycolide comprising a lactide, copolymer comprising a glycolic acid unit and a lactic acid unit or polylactic acid, a carboxylic acid group may be further introduced into the molecular chain in addition to the foregoing process. In some detail, a glycolide and a lactide are allowed to undergo ring-opening polymerization with a dihydroxycarboxylic acid as an initiator in the presence of a ring-opening polymerization catalyst.

In this manner, one or more carboxylic groups can be introduced into the polyester chain midway between the ends thereof. Examples of the dihydroxycarboxylic acid employable herein include 2,2-dimethylolpropionic acid, and dioxyadipic acid.

Referring to the reaction mechanism, the ring-opening polymerization catalyst is oriented toward the hydroxyl group faster than toward the carboxyl group. Thus, the ring-opening polymerization begins with the dihydroxy end, leaving the carboxyl group behind in the polymer chain.

As the lactone-based polyester there may be used a copolymer obtained by the ring-opening polymerization of lactones such as γ-butyrolactone, δ-vallelolactone and ε-caprolactone or the ring-opening addition polymerization of these lactones with polyester or polyether polyol.

The addition of a carboxylic acid group to the hydroxyl group in the lactone-based polyester can be accomplished by adding a polyvalent carboxylic acid or anhyride or chloride thereof to the terminal hydroxyl group in the lactone-based polyester so that the terminal is esterified to have a carboxyl group. This process can be effected in the same manner as described with reference to aliphatic polyester. In order to further enhance the acid value of the lactone-based polyester, lactones may be subjected to ring-opening polymerization with a dihydroxycarboxylic acid as an initiator in the presence of a ring-opening polymerization catalyst in the same manner as mentioned above.

Referring to the preparation of a polyester from a glycolide, lactide or lactone, a small amount of a polyol may be added to control the molecular weight of the polyester. This process can be applied also to the termination of the resulting polyester by hydroxyl group.

Specific examples of the polyol employable herein include ethylene glycol, propylene glycol, neopentyl glycol, 1,4-butylene glycol, pentaerythritol, glycerin, dimethylolpropionic acid, and dihydroxyadipic acid.

As the catalyst to be used in the foregoing reaction there may be used any compound generally known as ring-opening polymerization catalyst. Examples of the catalyst employable herein include alkoxide, acetate, oxide and chloride of Sn, Ti, Zn, Ge, Co, Fe, Al, Mn, etc. Preferred among these catalysts are tin octylate, dibutyltin dilaurate, tetraisopropyl titanate, tetrabutoxy titanium, titanium oxyacetylacetonate, ferric (III) acetylacetonate, ferric (III) ethoxide, aluminum isopropoxide, and aluminum acetylacetonate, which allow rapid reaction. The amount of the catalyst to be used is normally from 10 to 1,000 ppm, preferably from 50 to 500 ppm.

The number-average molecular weight of the biodegradable polyester to be used herein is preferably from 2,000 to 100,000, more preferably from 3,000 to 40,000, even more preferably from 5,000 to 30,000 taking into account the ease of introduction of carboxyl group.

The biodegradable polyester to be used in the present invention may be subjected to volatilization under reduced pressure or washing with a solvent before or after the introduction of carboxyl group so that the monomer remaining in the polyester is removed therefrom to retain the storage stability of the particulate material thus prepared. The residual monomer can cause odor or denature the particles if eluted into the aqueous phase side after the preparation of particles.

Though depending on the purpose of the particulate material, the residual monomer such as glycolide and lactide is not desired because it tends to generally cause hydrolysis by attachment of water content or fusion by heat. Accordingly, the content of the residual monomer is preferably not more than 1% by weight, more preferably not more than 0.5% by weight.

The polyvalent carboxylic acid or anhydride or chloride thereof left unreacted in the polyester after the introduction of carboxyl group can cause the hydrolysis of the polyester main chain. Thus, it is preferred that the polyester be subjected to volatilization under reduced pressure or washing with a solvent to remove the unreacted residual materials therefrom.

The acid value of the biodegradable polyester having carboxyl groups to be used in the present invention is preferably from 4 to 200 KOHmg/g, more preferably from 10 to 200 KOHmg/g, even more preferably from 20 to 200 KOHmg/g.

If the acid value of the biodegradable polyester falls below 4 KOHmg/g, the resulting polyester exhibits a high hydrophobicity and thus can hardly undergo phase inversion emulsification, making it impossible to obtain fine particles.

On the contrary, if the acid value of the biodegradable polyester exceeds 200 KOHmg/g, the resulting polyester can hardly undergo phase inversion emulsification unless it has a number-average molecular weight of less than 2,000. However, if a polyester having a number-average molecular weight of less than 2,000 is used, the resin content is eluted into the aqueous phase side more during phase inversion emulsification to disadvantage.

The number-average molecular weight of the polyester having acid groups to be used in the present invention is from 2,000 to 100,000, preferably from 3,000 to 50,000, more preferably from 5,000 to 30,000 to sufficiently accomplish the properties of the resin in particulate form.

If the number-average molecular weight of the polyester having acid groups falls below 2,000, the resin content is eluted into the aqueous phase side more during phase inversion emulsification. Further, the resulting particulate resin can sufficiently maintain its desired properties, i.e., strength. On the contrary, if the number-average molecular weight of the polyester having acid groups exceeds 100,000, it is made impossible to raise the acid value of the polyester to not less than 4 KOHmg/g. Further, when it comprises water added thereto, the resulting polyester exhibits a raised viscosity that hinders phase inversion emulsification.

The process for the preparation of the self-water dispersible particle made of a biodegradable polyester will be further described hereinafter. In some detail, a base is added to a biodegradable polyester which has carboxyl groups incorporated therein by the foregoing process to neutralize the carboxylic acid and hence provide the polyester with a neutralized salt structure. During this procedure, the reaction mixture is preferably diluted with a proper solvent to improve the working efficiency, i,e, reduce the viscosity of the resin solution.

Examples of the base to be used as a neutralizing agent herein include inorganic base such as alkali (e.g., sodium hydroxide and potassium hydroxide, carbonate and acetate thereof) and aqueous ammonia, and organic base such as alkylamine (e.g., methylamine, dimethylamine, trimethylamine, ethylamine, diethylamine, triethylamine), alkanolamine (e.g., dimethyl ethanolamine, diethanolamine) and alkylammonium hydroxide (e.g., tetramethylammonium hydroxide, tetraethylammonium hydroxide).

Examples of the solvent to be used for dissolving the biodegradable polyester having carboxyl groups incorporated therein include chlorine-based organic solvent such as methylene chloride and chloroform, ketone-based organic solvent such as acetone and methyl ethyl ketone (hereinafter abbreviated as "MEK"), ether-based organic solvent such as tetrahydrofuran (hereinafter abbreviated as "THF"), ester-based organic solvent such as ethyl acetate, and alcohol-based organic solvent such as isopropyl alcohol. These solvents may be used singly or in combination. Since a biodegradable polyester having carboxyl groups incorporated therein is dispersed in water with an organic solvent, the organic solvent preferably has a relatively high affinity for water. Further, since the organic solvent must be removed after dispersion, the organic solvent preferably has a lower boiling point than water.

When water is added to an organic solvent solution of the polyester having a neutralized salt structure with stirring, the solution undergoes phase inversion emulsification leading to the formation of a particulate polyester. During this procedure, an organic solvent solution of the polyester having a neutralized salt structure may be added to water with stirring. Alternatively, an aqueous solution having a base dissolved therein may be added to an organic solvent solution of a polyester having carboxyl groups. In accordance with either of these processes, a particulate polyester can be similarly formed.

The addition of the foregoing components may be effected dropwise or at once. If the addition is effected at once, the self-water dispersible polyester used preferably has a high hydrophilicity. The term "hydrophilicity" as used herein is meant to indicate not only high acid value but also high hydrophilicity derived from the polyester structure. In practice, accordingly, the addition is preferably effected in some time, e.g., dropwise.

The agitation process during phase inversion emulsification will be further described hereinafter. The higher the agitation speed is, the smaller is the particle diameter of the resulting particulate material. However, the agitation speed has not so big effect on the resulting particle diameter as the acid value of the polyester. Therefore, the agitation speed may be arbitrary so far as the water or solution added can be rapidly diffused. Accordingly, this mechanism differs greatly from the prior art technique in which the agitation efficiency is important.

Referring to an experimental example of agitation operation, agitation at 400 rpm using a paddle having a length of 50 mm is enough if a 200 ml flask is used. Any agitating blade may be used so far as it is suitable for the agitation of a material having a viscosity ranging from a low value to a middle value. Specific examples of such an agitating blade, if used, include paddle agitator, propeller blade, anchor blade, fardler (??) blade, turbine impeller, maxblend blade, and full-zone blade.

One or more hydrophobic materials such as hydrophobic pesticide, pharmaceutical preparations and pigment to be used as hydrophobic core materials are dissolved or dispersed in the foregoing organic solvent solution of a biodegradable polyester having acid groups. The solution or dispersion thus obtained is then subjected to the same processing as mentioned above to obtain a particulate material, i.e., microcapsule having these hydrophobic core materials encapsulated therein.

The term "hydrophobic core material" as used herein is meant to indicate a material having a water solubility of not more than 10% by weight at 25° C. which doesn't dissolve or damage a biodegradable polyester. The hydrophilic core material preferably has a water solubility of not more than 1% by weight to make itself to be efficiently encapsulated in the particles.

The weight ratio of hydrophobic core material to biodegradable polyester in the particulate material of the present invention is preferably from 90/10 to 10/90, and more preferably from 80/20 to 30/70, particularly from 75/25 to 50/50 taking into account the strength of particles.

The hydrophilic core material is preferably soluble in the organic solvent solution of a biodegradable polyester having acid groups. However, the solubility in the organic solvent is not essential. In practice, any hydrophilic core material which can be finely dispersed in the organic solvent may be used. Examples of such a dispersible hydrophilic core material include carbon black, silicon oxide, calcium carbonate, clay, and talc.

By changing the rate of neutralization of the acid group in the biodegradable polyester with a base (percent neutralization), i.e., changing the amount of the neutralized salt structure (hereinafter referred to as "neutralized acid value"), the degree of water dispersibility can be controlled, making it possible to adjust the particle diameter of the resulting particulate material. The greater the percent neutralization is, i,e., the greater the neutralized acid value is, the smaller is the resulting average particle diameter. This is because the resulting polymer exhibits an enhanced hydrophilicity and thus can be finely dispersed in water.

The foregoing percent neutralization is normally from 20% to 100%. However, if the neutralized acid value is too high, the polymer exhibits too high a hydrophilicity and thus is lost away in water, resulting in the drop of the yield of the particles thus produced to disadvantage. Accordingly, the neutralized acid value is preferably from 4 to 150 KOHmg/g, more preferably from 5 to 100 KOHmg/g.

The biodegradable polyester of the present invention preferably has an acid value of from 4 to 200 KOHmg/g, more preferably from 10 to 200 KOHmg/g, more preferably from 20 to 200 KOH mg/g as mentioned above.

The acid value of the biodegradable polyester is preferably as high as possible to obtain a particulate material having a small average particle diameter and a sharp particle size distribution. Further, by enhancing the acid value of the biodegradable polyester used as much as possible and suppressing the percent neutralization and neutralized acid value, a particulate material having a small particle diameter and a sharp particle size distribution can be obtained.

As mentioned above, by changing the production conditions of the present invention, the average particle diameter of the particulate material thus obtained can be varied within a wide range of from several nanometer to several micrometer, even to several millimeter. In practice, however, the average particle diameter of the particulate material thus obtained is normally from 0.01 to 500 µm, preferably from 0.01 to 100 µm, more preferably from 0.1 to 100 µm taking into account the ease of production.

The particulate polyester which has undergone phase inversion emulsification is obtained in the form of aqueous dispersion containing a small amount of an organic solvent. Depending on the purpose, the aqueous dispersion may be used as it is or may be freed of organic solvent by distillation under reduced pressure to give an aqueous dispersion free of organic solvent which is then used. Further, the particulate material may be filtered off or the like methods, and then dried to obtain a powder which is then used. During this procedure, the particulate material may be washed with water or an organic solvent as necessary.

If used in powder form, the aqueous dispersion of particulate polyester may be directly dried by spray drying method to form a powder. Alternatively, if the particle diameter of the particulate polyester is relatively large, the particulate material may be directly filtered off to obtain a wet cake which is then dried by an ordinary method such as vacuum drying to form a powder.

In either case, the organic solvent is preferably distilled off under reduced pressure before spray drying or withdrawal by filtration to prevent the mutual fusion of particles. Further, the particulate material may be reverse-neutralized with a proper acid to lower the self-water dispersbility thereof so that it can be agglomerated and then filtered off. In this case, too, the organic solvent is preferably distilled off under reduced pressure before reverse neutralization to prevent the mutual fusion of resin particles.

If the aqueous dispersion of a self-water dispersible particle having a hydrophobic core material encapsulated therein is allowed to stand over a long period of time, the dispersion stability of the aqueous dispersion can be deteriorated to cause precipitation of particles. The deterioration of dispersion stability is attributed to the fact that the hydrophobic core material in the particulate material is soluble in an organic solvent but has a low miscibility with a resin and is crystallizable and thus is pushed out of the particulate material to grow in crystalline form outside the particulate material.

In order to prevent the deterioration of dispersion stability, a slight amount of a crystallization nucleating agent may be added during the dispersion of the biodegradable polyester and the hydrophobic core material in water to cause the crystallization of the hydrophobic core material in the particulate material with the nucleating agent incorporated in the particulate material as a nucleus, making it possible to enhance the stability of the aqueous dispersion of particles thus obtained.

The amount of the nucleating agent to be added is preferably from 0.01 to 5% by weight based on the weight of the hydrophobic core material used. The crystallization speed is affected by the added amount of the nucleating agent. Thus, if the added amount of the nucleating agent exceeds 5% by weight, crystallization proceeds rapidly before the formation of particles, remarkably deteriorating the working efficiency to disadvantage. On the contrary, if the added amount of the nucleating agent falls below 0.01%, the desired effect of enhancing dispersion stability by nucleating agent cannot be exerted.

The nucleating agent employable herein is not specifically limited so far as it is nonreactive and smaller than the particles. In practice, however, silicon dioxide or titanium oxide is preferably used. More preferably, particulate silicon dioxide or titanium oxide having a particle diameter of from 10 nm to 300 nm is used. Alternatively, there may be used a particulate nucleating agent which has been surface-modified so that the surface of the particulate nucleating agent is rendered hydrophilic or hydrophobic or taking into account the crystal growth speed.

The self-water dispersible particle made of a biodegradable polyester obtained according to the present invention is biodegradable and thus cannot remain even if discarded in the environment. Microcapsules comprising hydrophobic pesticide, pharmaceutical preparations or the like encapsulated therein as hydrophobic core materials exhibit gradual releasability due to gradual decomposition, i.e., so-called biodegradation in natural world or living body and thus can not only be used as pesticide or pharmaceutical preparations but also find wide application such as coating, ink, toner, adhesive, lamination for paper, foaming resin material, fire extinguishing agent, cosmetic material, construction material, etc.

The pesticide activator as an example of the hydrophobic core materials will be described hereinafter.

Examples of the pesticide activator employable herein include fungicide, insecticide, herbicide, attractant for attracting and killing insect pests, repellent against insect pests and birds, and growth promoting agent or germinating inhibitor for promoting or inhibiting the physiological function of farm products. Any hydrophobic pesticide activators may be used. Examples of these pesticide activators will be given below.

Examples of insecticide are shown as described below;
N,N-bis(2,4-xylyliminomethyl)methylamine (amitraz),
(RS)-3-allyl-2-methyl-4-oxocyclopent-2-enyl(1RS)cis, trans-2,2-dimethyl-3-(2-methyl-1-propenyl) cyclopropanecarboxylate (allethrin),
O,O-diethyl-O-(5-phenyl-isoxazol-3-yl)phosphorothioate (isoxathion),
O-ethyl-O-2-isopropoxycarbonylphenyl-isopropylphosphoramidothioate (isofenphos),
O,O-diethyl-S-2-ethylsulfonylethylphosphorodithioate (ethylthiometon),
2-(4-ethoxyphenyl)-2-methylpropyl-3-phenoxybenzyl-ether (ethofenprox),
N,N-dimethyl-2-methylcarbamoyl-oxyimino-2-(methylthio)acetamide (oxamyl), 2,3-dihydro-2,2-dimethylbenzofuran-7-yl(dibuthylaminothio) methylcarbamate (carbosulfan),
O,O-diethyl-O-quinoxalin-2-yl-phosphorothioate (quinalphos),
6-methylquinoxalin-2,3-dithiocarbanate (quinoxaline),
trichloromethane (chloropicrin),
O,O-dimethyl-O-3,5,6-trichloro-2-pyridylphosophrothioate (chlorpyrifos-methyl),
1-[3,5-dichloro-4-(3-chloro-5-trifluoromethyl-2-pyridyloxy)phenyl]-3-(2,6-difluoro-benzoyl)urea (chlorfluazuron),
ethyl-4,4'-dichlorobenzilate (chlorobenzilate),
2,2,2-trichloro-1,1-bis(4-chlorophenyl) (kelthane),
2-methoxy-4H-1,3,2-benzodioxaphosphorin-2-sulfide (salithion),
perchloro-1,1'-bi(cyclopenta-2,4-diene (dienochlor),
(RS)-α-cyano-3-phenoxybenzyl(RS)-2,2-dichloro-1-(4-ethoxyphenyl)cyclopropane-carboxylate (cycloprothrin),
(RS)-α-cyano-3-phenoxybenzyl(Z)-(1RS,3RS)-3-(2-chloro-3,3,3-trifluorophenyl)-2,2-dimethylcyclopropanecarboxylate (cyhalothrin),
(RS)-α-yan-4-fluoro-3-phenoxybenzyl(1RS,3RS)-(1RS,3SR)-3-(2,2-dichlorovinyl)-2,2-dimethylcyclopropanecarboxylate (cyfluthrin),
1-(4-chlorophenyl)-3-(2,6-difluorobenzoyl)urea (diflubenzuron),
(R,S)-α-cyano-3-phenoxybenzyl(1RS,3RS)-(1RS,3SR)-3-(2,2-dichlorovinyl)-2,2-dimethylcyclopropanecarboxylate (cypermethrin),
2-chloro-1-(2,4-dichlorophenyl)vinyldimethylphosphate (dimethylvinphos),
O-ethyl-O-(4-methylthiophenyl)-S-propylphosphorodithioate (sulprofos),
O,O-diethyl-O-2-isopropyl-6-methylpyrimidin-4-yl-phosphorothioate (diazinon), 3,7,9,13-tetramethyl-5,11-dioxa-2,8,14-trithia-4-7-9-12-tetraazapentadeca-3,12-diene-6,10-dione (thiodicarb),
O,O-dimethyl-S-2-ethylthioethyldithiophosphate (thiometon),
(RS)-[O-1-(4-chlorophenyl)pyrazol-4-yl-O-ethyl-S-proypylphosphorothioate (pyraclofos),
O,O-diethyl-O-(2,3-dihydro-3-oxo-2-phenyl-6-pyridazinyl) phosphorothioate (pyridaphenthion),
Isopropyl-4,4'-dibromobenzilate (bromopropylate),
S-4-(phenoxybuthyl)dimethylthiocarbamate (fenothiocarb),
(RS)-α-cyano-phenoxybenzyl(RS)-α-isopropyl-4-chlorophenylacetate (fenvalerate),
(RS)-α-cyano-3-phenoxybenzyl-2,2,3,3-tetramethylcyclopropanecarboxylate (fenpropathrin),
2-tert-butylimino-3-isopropyl-5-phenyl-1,3,5-thiadiazinan-4-one (buprofezin), (RS)-α-cyano-3-phenoxybenzyl-(S)-2-(4-difluoromethoxyphenyl)-3-methyl-butyrate (flucythrinate),
(RS)-α-cyano-3-phenoxybenzyl-N-(2-chloro-α,α,α-trifluoro-p-tolyl)-D-valinate (fluvalinate),
O-2,4-dichlorophenyl-O-ethyl-S-propylphosphorodithioate (prothiofos),
O-(4-bromo-2-chlorophenyl)-O-ethyl-S-propylphosphorothioate (profenofos), (4RS,5RS)-5-(4-chlorophenyl)-N-cyclohexyl-4-methyl-2-oxo-1,3-thiazolidine-3-carboxamide (hexythiazox),
S,S'-2-dimethylaminotrimethylene-di (benzenethiosulfonate) (bensultap),
6,7,8,9,10,10-hexachloro-1,5,5a, 6,9,9a-hexahydro-6,9-methano-2,4,3-benzodioxathiepin-3-oxide (endosulfan),
3-chloro-α-ethoxyimino-2,6-dimethoxybenzylbenzoate (benzoximate),
2,2-dimethyl-1,3-benzodioxol-4-yl-methylcarabamate (bendiocarb),
ethyl-N-[2,3-dihydro-2,2-dimethylbenzofuran-7-yl-oxycarbonyl(methyl)-aminothio]-N-isopropyl-β-alaninate (benfuracarb),
S-6-chloro-2,3-dihydro-2-oxobenzoxazol-3-ylmethyl-O,O-diethyl-phosphoro-dithioate (phosalone),
S-(N-formyl-N-methylcarbamoylmethyl)-O,O-dimethylphosphorodithioate (formothion),
(S)-1,2-bis(ethoxycarbonyl)ethyl-O,O-dimethylphosphorodithioate (malathion), dimethyl(E)-1-methyl-2-(methylcarbamoyl)-vinylphosphate (monocrotophos),
bis [tris(2-methyl-2-phenylpropyl)tin]oxide (fenbutatin oxide),
1,2-dibromo-2,2-dichloroethyl dimethyl phosphate (BRP),
4-chlorophenyl-4-chlorobenzenesulfonate (CPCBS),
2-chloro-1-(2,4-dichlorophenyl)vinyl-diethylphosphate (CVP),
O-(4-cyanophenyl)-O,O-dimethyl phosphorothioate (CYAP),
2,2-dichlorovinyl dimethyl phosphate (DDVP),
S-2,3-dihydro-5-methoxy-2-oxo-1,3,4-thiadiazol-3-ylmethyl-O,O-dimethyl phosphorodithioate (DMTP),
O-2,4-dichlorophenyl-O,O-diethyl phosphorothioate (ECP),
O-ethyl-O-p-nitrophenyl phenylphosphonothioate (EPN),
O,O-dimethyl O-4-nitro-m-tolyl phosphorothioate (MEP),
3,4-xylyl methylcarbamate (MPHC),
O,O-dimethyl O-4-methylthio-m-tolyl phosphorothioate (MPP),
1-naphthyl methylcarbamate (NAC),
S-α-ethoxycarbonylbenzyl-O,O-dimethyl phosphorodithioate (PAP),
2-isopropoxyphenyl methylcarbamate (PHC),
O,O-dimethyl-S-phthalimidomethyl phosphorodithioate (PMP),
3,5-xylyl methylcarbamete (XMC).

Examples of fungicide are shown as described below;
diisopropyl-1,3-dithiolan-2-ylidenemalonate (isoprothiolane),
3-(3,5-dichlorophenyl)-N-isopropyl-2,4-dioxoimidazoline-1-yl-carboxamide (iprodione),
ethyl-3-trichloromethyl-1,2,4-thiazol-5-ylether (etridiazole), 2-methoxy-N-(2-oxo-1,3-oxazolidine-3-yl)acetamide-2',6'-xylidine (oxadixyl),
5,6-dihydro-2-methyl-1,4-oxathiin-3-carboxanilide-4,4-dioxide (oxycarboxin), methyl benzimidazol-2-ylcarbamate (carbendazim),
N-(trichloromethylthio)cyclohex-4-ene-1,2dicarboximide (captan),
1,4-dichloro-2,5-dimethoxybenzene (chloroneb),
6-(3,5-dichloro-p-tolyl)pyridazin-3(2H)-one (diclomezin),
5,10-dihydro-5,10-dioxonaphtho[2,3-b]-1,4-dithiin-2,3-dicarbonitrile (dithianon), 5-butyl-2-(dimethylamino)-6-methylpyrimidin-4-ol (dimethirimol),
N-dichloroflioromethylthio-N',N'-dimethyl-N-phenylsulfamide (dichlofluanid), tetrahydro-3,5-dimethyl-1,3,5-thiadiazin-2-thione (dazomet),
2-thiazol-4-ylbenzimidazole (thiabendazole),
tetramethylthiuram disulfide (thiram),
dimethyl-4,4-(o-phenylene)-bis(3-thioallophanate) (thiophanate-methyl),
2,4-dichloro-6-(2-chloroanilino)-1,3,5-triazine (anilazine),
O-2,6-dichloro-p-tolyl-O,O-dimethyl (tolclophos-methyl),
5-methyl-1,2,4-triazolo[3,4-b]benzothiazole (tricyclazole),
(E)-4-chloro-α,α,α-trifluoro-N-(1-imidazol-1-yl-2-propoxy-ethilidene)-o-toluidine (triflumizole),
1,4-bis(2,2,2-trichloro-1-formamidoethyl)piperazine (triforine),
O-6-ethoxycarbonyl-5-methylpyrazolo[1,5-a]-pyrimidin-2-yl-O,O-diethyl-phosphorothioate (pyrazophos),
3-(3,5-dichlorophenyl)-5-methyl-5-vinyl-1,3-oxazolidine-2,4-dione (vinclozolin), 2,4'-dichloro-α-(pyrimidin-5-yl)benzhydrylalcohol (fenarimol),
2,3-dichloro-4-fluorophenylmaleimide (fluoroimide),
α,α,α-trifluoro-3'-isopropoxy-o-toluanilide (flutoluanil),
N-(3',5'-dichlorophenyl)-1,2-dimethylcyclopropane-1,2-dicarboxyimide (procymidone),
methyl-3-butylcarbamoyl-3H-benzimidazol-2-ylcarbamate (benomyl), iminoctadine-albesilate, 1-(4-chlorobenzyl)-1-cyclopentyl-3-phenylurea (pencycuron),
2-(thiocyanomethylthio)-1,3-benzothiazole (benthiazole),
methyl-N-(2-methoxyacetyl)-N-(2,6-xylyl)-DL-alaninate (metalaxyl),
3'-isopropoxy-o-toluanilide (mepronil),
2,6-dichloro-4-nitroaniline (CNA),
2,4(6)-dinitro-6(4)-octylphenyl crotonates (DPC),
O-ethyl-S,S-diphenyl phosphorodithioate (EDDP),
pentachloronitrobenzene (PCNB),
tetrachloro-isophthalonitrile (TPN).

Examples of herbicide are shown as described below;
methyl sulfanilycarbamate (asulam),
2-chloro-4-ethylamino-6-isopropylamino-1,3,5-triazine (atrazine),
O-methyl O-2-nitro-p-tolyl isopropylphosphoramidothioate (amiprophos-methyl), 2-ethylamino-4-isopropylamino-6-methylthio-1,3,5-triazine (ametryn),
2-chloro-2',6'-diethyl-N-(methoxymethyl)acetanilide (alachlor),
3-(5-tert-butyl-3-isoxazolyl)-1,1-dimethylurea (isouron),
S-benzyl-N-(1,2-dimethlpropyl)-N-ethylthiocarbamate (esprocarb),
1-(5-ethylsufonyl-1,3,4-thiadiazol-2-yl)-1,3-dimethylurea (ethidimuron),
5-tert-butyl-3-(2,4-dichloro-5-isopropoxyphenyl)-1,3,4-oxadiazol-2(3H)-one (ozadiazon),
3-(3,3-dimethylureido)phenyl tert-butylcarbamate (karbutilate),
5-(2,dichlorophenoxy)-2-nitroanisole (chlomethoxyfen),
(RS)-2-(2,4-dichloro-m-tolyloxy)propionanilide (chlomeprop),
2-(1-cyano-1-methylethylamino)-4-ethylamino-6-chloro-1,3,5-triazine (cyanazin), S,S-dimethyl 2-difluoromethyl-4-isobutyl-6-trifluoromethyl-3,5-pyridine-dicarbothioate (dithiopyr),
N,N-dimethyl-2,2-diphenylacetamide (diphenamid),
2-(1,2-dimethylpropylamino)-4-ethylamino-6-methylthio-1,3,5-triazine (dimethametryn), 2,4-bis(ethylamino)-6-methylthio-1,3,5-triazine (simetryn),
S-1-methyl-1-phenylethylpiperidine-1-carbothioate (dimepiperate),
1-(α,α-dimethylbenzyl)-3-(p-tolyl)urea (dymron), 1,3-dimethyl-1-(5-trifluoro-methyl-1,3,4-thiadiazol-2-yl)urea (thiazafluron),
2-chloro-N-(3-methoxy-2-thenyl)-2',6'-dimethylacetanilide (thenylchlor),
2-(β-naphthyloxy)propionanilide (naproanilide),
N,N-diethyl-2-(α-naphthyloxy)propionamide (napropamide),
Methyl 5-(2,4-dichlorophenoxy)-2-nitrobenzoate (bifenox),
S-2-methylpiperidinocarbonylmethyl O,O-di-n-propylphosphorodithioate (piperophos),
2-[4-(2,4-dichlorobenzoyl)-1,3-dimethylpyrazol-5-yloxy] acetophenone (pyrazoxyfen),
4-(2,4-dichlorobenzoyl)-1,3-dimethylpyrazol-5-yloxytoluene-4-sulfone (pyrazolate), O-3-tert-butylphenyl N-(6-methoxy-2-pyridyl)-N-methylthiocarbamate (pyributycarb),
ethyl 2-[4-(6-chloro-2-benzoxazolyloxy)phenoxy] propionate (phenoxaprop-ethyl), S-ethyl 4-chloro-2-methylphenoxythioacetate (phenothiol),
methyl-3-(3-methylcarbaniloyloxy)carbanilate (phenmedipham),
2-chloro-2',6'-diethyl-N-(butoxymethyl)acetanilide (butachlor),
O-ethyl O-6-nitro-m-tolyl-sec-butylphosphoramidothioate (butamifos),
butyl(RS)-2-[4-(5-trifluoromethyl-2-pyridyoxy)phenoxyl] propionate (fluazifop-butyl),
2-chloro-2',6'-diethyl-N-(2-propoxyethyl)acetanilide (pretilachlor),
3,5-dichloro-N-(1,1-dimethyl propynyl)benzamide (propyzamide),
5-bromo-3-sec-butyl-6-methyluracil (bromacil),
2,4-bis(isoprpylamino)-6-methylthio-1,3,5-triazine (prometryn),
N,N-dibutyl-2,6-dinitro-4-trifluoromethylaniline (beslogine),
3-(4,6-dimethoxypyrimidin-2-yl)-1-[(2-methoxycarbonylbenzyl)sulfonyl]urea (bensulfuronmethyl), 3-isoprpyl-1H-2,1,3-benzothiadiazin-4(3H)-one-2,2-dioxide (bentazone),
S-4-chlorobenzyl diethylthiocarbamate (thiobencarb),
N-(1-ethylpropyl)-2,6-dinitro-3,4-xylidine (pendimethalin),
1-(α,α-dimethylbenzyl)-3-methyl-3-phenylurea (methyldymron),
2-chloro-6'-ethyl-N-(2-methoxy-1-methylethyl)acet-o-toluidine (metolachlor),
4-amino-6-tert-butyl-3-methylthio-1,2,4-triazin-5(4H)-one (metribuzin),
2-benzothiazol-2-yloxy-N-methyl-acetoanilide (mefenacet),
S-ethyl perhydroazepin-1-carbothioate (molinate),
3-(3,4-dichlorophenyl)-1-methoxy-1-methylurea (linuron),
3-cyclohexyl-6,7-dihydro-1H-cyclopentapyrimidin2,4(3H,5H)-dione (lenacil),
2,4-dichlorophenoxyacetate (2,4-PA),
2-chloro-4,6-bis(ethylamino)-1,3,5-triazine (CAT),
2,4,6-trichlorophenyl-4'-nitrophenylether (CNP), 2,6-dichlorobenzonitrile (DBN), 2,6-dichlorothiobenzamide (DCBN),
3-(3,4-dichlorophenyl)-1,1-dimethylurea (DCMU),
N-(4-chlorophenyl)-3,4,5,6-tetrahydrophthalimide (chlorphtalim),
Isopropyl carbanilate (IPC), 2,6-di-tert-butyl-p-tolyl methylcarbamate (MBPMC), methyl(3,4-dichlorophenyl) carbamate (MCC),
4-(4-chloro-o-tolyloxy)butyric acid (MCPB), 3,6-dichloro-o-anisic acid (MDBA),
5-amino-4-chloro-2-phenylpyridazin-3(2H)-one (PAC), dimethyl=2,3,5,6-tetrachloroterephthalate (TCTP).

EXAMPLES

The present invention will be further described in the following examples and comparative examples, but the present invention should not be construed as being limited thereto.

For the determination of the molecular weight of polyether polyol, end-group analysis was employed. For the determination of the molecular weight of other compounds, a gel permeation chromatography (hereinafter abbreviated as "GPC"; Type HLC-8020, produced by TOSOH CORP.; column temperature: 40°C.; solvent: tetrahydrofuran) was employed. The measurements were then compared with the results of polystyrene standard sample.

For the measurement of the average particle diameter of microcapsules, MICROTRAC UPA150 (produced by NIKKISO CO., LTD.) was employed. For the measurement of acid value, the polyester was dissolved in a solvent. The solution thus obtained was then alkalinically titrated with a 0.1 N alcohol solution of KOH to determine the acid value. For the optical observation of particles, OPTIPHOTO (optical microscope produced by NIKON CORP.) was used. The examination was effected at a magnification of ×1,250.

Example 1

Into a 1 liter separable four neck flask equipped with an agitator, a fractionating column and a nitrogen gas intake pipe were charged 404.6 g of sebasic acid, 100.0 g of ethylene glycol and 118.2 g of 1,6-hexanediol. In an atmosphere of nitrogen, the reaction components were melt-mixed at a temperature of 150° C. for 0.5 hour, and then stirred while being heated at a rate of 10° C./hr.

The reaction mixture was then heated to a temperature of 220° C. while water produced was being distilled off. After 8 hours, to the reaction solution was added 0.015 g of titanium tetrabutoxide. The reduction of the pressure in the reaction system was then allowed to begin. After 2 hours, the pressure in the reaction system was reduced to 0.1 Pa. The reaction solution was then allowed to undergo deglycolation reaction at a temperature of 220° C. for 5 hours. The aliphatic polyester thus obtained had a number-average molecular weight of 28,000 and a weight-average molecular weight of 56,000 (hereinafter simply referred as "P1").

Into a 200 ml separable three neck flask equipped with an agitator, a fractionating column and a nitrogen gas intake pipe were charged 69.3 g of L-lactide, 0.7 g of D-lactide, 30.0 g of (P1), 2.0 g of ethylene glycol and 20 ml of toluene. In an atmosphere of nitrogen, the reaction components were melt-mixed at a temperature of 175° C. for 0.5 hour. To the reaction mixture was then added 0.03 g of tin octanoate. After 3 hours of reaction, the resulting polymer was sampled and measured for molecular weight Mn. The results were 6,200.

To the polymer was then added 6.21 g of pyromellitic anhydride (hereinafter abbreviated as "PMDA"). The pressure in the reaction system was then reduced to 1 Pa at a temperature of 183° C. for 6hours. The lactic acid-based polyester copolymer thus obtained exhibited a number-average molecular weight of 7,500 and Mw of 20,000. The lactic acid-based polyester copolymer was dissolved in chloroform, and then reprecipitated with methanol so that it was purified. The polymer thus obtained exhibited Mn of 16,000, Mw of 25,000 and an acid value of 14 KOHmg/g.

Subsequently, into a 300 ml three neck round flask equipped with an anchor agitator were charged 10 g of the polymer thus purified and 50.0 g of methylene chloride. The reaction components were dissolved with stirring, and then neutralized with 1.9 g of triethylamine (to a neutralization of 100%). To the reaction solution was then 1.6 g of 2-propanol. The agitation speed was raised to 400 rpm where 200 ml of distilled water was then added dropwise to the reaction solution in 20 minutes to cause phase inversion emulsification.

Figure 2:
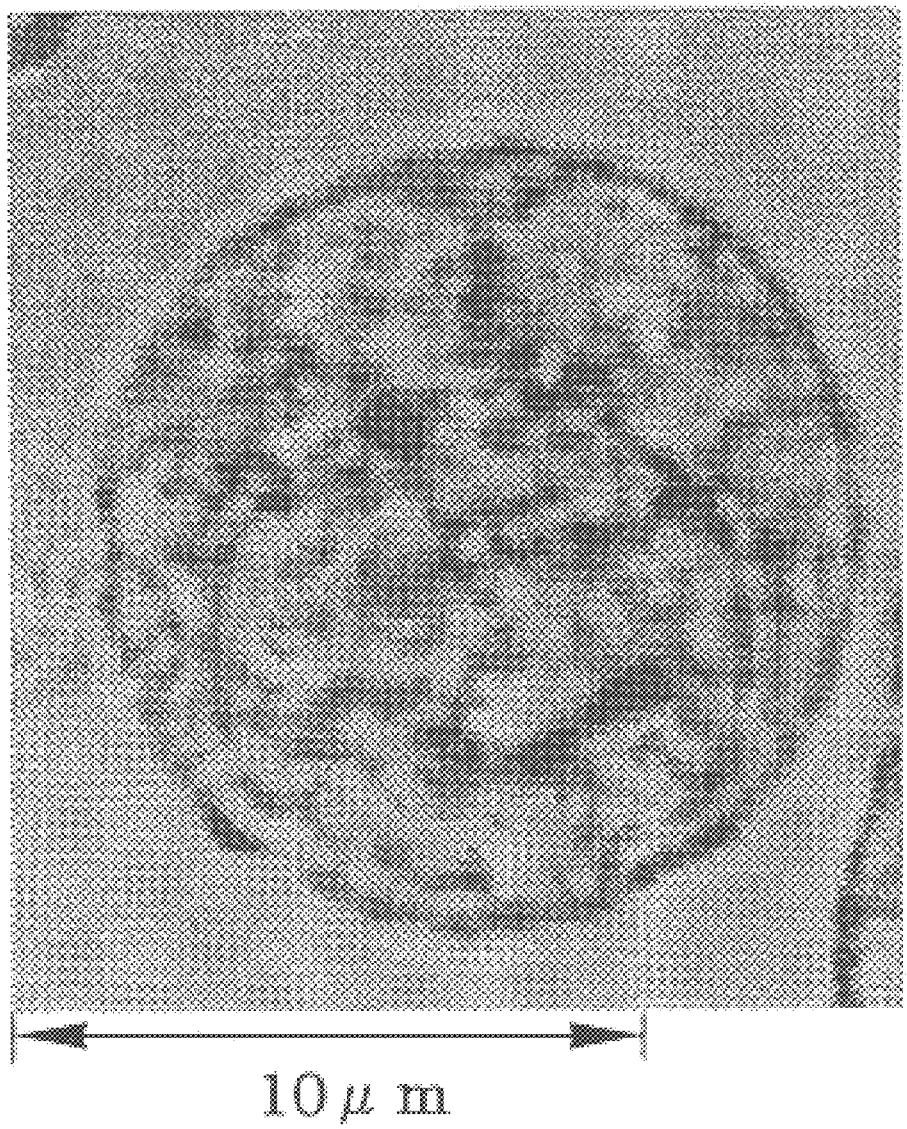
FIG. 2 is an optical microphotograph (magnification of ×1,250) of the self-water dispersible particle made of a biodegradable polyester prepared in Example 1.

The reaction solution was then distilled at a temperature of 35° C. under reduced pressure for 1 hour to remove methylene chloride therefrom. Thus, an aqueous dispersion comprising particles was obtained. The particles were filtered off, washed with water, and then dried at a temperature of 30° C. under reduced pressure for 4 hours to obtain particles having an average particle diameter of 20 μm. Even after dried, the particles underwent neither agglomeration nor blocking. An optical microphotograph of the aqueous-dispersed particles thus obtained is shown in FIG. 2 at a 1,250× magnification.

Example 2

Into a 1 liter separable four neck flask equipped with an agitator, a fractionating column and a nitrogen gas intake pipe were charged 404.6 g of sebasic acid and 167.6 g of ethylene glycol. In an atmosphere of nitrogen, the reaction components were melt-mixed at a temperature of 150° C. for 0.5 hour, and then stirred while being heated at a rate of 10° C./hr. The reaction mixture was then heated to a temperature of 220° C. while water produced was being distilled off. After 8 hours, the reaction product was taken out. The aliphatic polyester thus obtained had a number-average molecular weight of 3,000 and a weight-average molecular weight of 4,400 (hereinafter simply referred as "P2").

Into a 200 ml separable three neck flask equipped with an agitator, a fractionating column and a nitrogen gas intake pipe were charged 70.0 g of L-lactide, 30.0 g of the polyester (P2) and 20 ml of toluene. In an atmosphere of nitrogen, the reaction components were melt-mixed at a temperature of 175° C. for 0.5 hour. To the reaction mixture was then added 0.03 g of tin octanoate. After 3 hours of reaction, the resulting polymer was sampled and measured for molecular weight Mn. The results were 7,000. To the polymer was then added 3.55 g of PMDA. The pressure in the reaction system was then reduced to 1 Pa at a temperature of 185° C. for 2 hours. The lactic acid-based polyester copolymer thus obtained exhibited Mn of 7,200 and Mw of 14,000. The lactic acid-based polyester copolymer was dissolved in chloroform, and then reprecipitated with methanol so that it was purified. The polymer thus obtained exhibited Mn of 9,200, Mw of 15,000 and an acid value of 21 KOHmg/g.

Subsequently, into a 300 ml three neck round flask equipped with an anchor agitator were charged 10 g of the polymer thus purified and 6.5 g of methyl ethyl ketone. The reaction components were dissolved with stirring, and then neutralized with 2.6 g of a 0.1 N aqueous solution of sodium hydroxide (to a neutralization of 100%). To the reaction solution was then 2.5 g of 2-propanol. The agitation speed was raised to 500 rpm where 200 ml of distilled water was then added dropwise to the reaction solution in 30 minutes to cause phase inversion emulsification. The reaction solution was then distilled at a temperature of 35° C. under reduced pressure for 1 hour to remove methyl ethyl ketone therefrom. The particles thus obtained were filtered off, washed with water, and then dried at a temperature of 30° C. under reduced pressure for 5 hours to obtain particles having an average particle diameter of 5 jam. Even after dried, the particles underwent neither agglomeration nor blocking.

Example 3

Into a 1 liter separable four neck flask equipped with an agitator, a fractionating column and a nitrogen gas intake pipe were charged 344.4 g of adipic acid and 160.0 g of ethylene glycol. In an atmosphere of nitrogen, the reaction components were melt-mixed at a temperature of 150° C. for 0.5 hour, and then stirred while being heated at a rate of 10° C./hr. The reaction mixture was then heated to a temperature of 220° C. while water produced was being distilled off. After 8 hours, the reaction product was taken out. The aliphatic polyester thus obtained had a number-average molecular weight of 3,100 and a weight-average molecular weight of 4,100 (hereinafter simply referred as "P3").

Into a 200 ml separable three neck flask equipped with an agitator, a fractionating column and a nitrogen gas intake pipe were charged 92.0 g of L-lactide, 8.0 g of the polyester (P3) and 20 ml of toluene. In an atmosphere of nitrogen, the reaction components were melt-mixed at a temperature of 175° C. for 0.5 hour. To the reaction mixture was then added 0.05 g of tin octanoate. After 3 hours of reaction, the resulting polymer was sampled and measured for molecular weight Mn. The results were 31,000. To the polymer was then added 2.20 g of PMDA. The pressure in the reaction system was then reduced to 1 Pa at a temperature of 185° C. for 2 hours. The lactic acid-based polyester copolymer thus obtained exhibited Mn of 30,000 and Mw of 44,000. The lactic acid-based polyester copolymer was dissolved in chloroform, and then reprecipitated with methanol so that it was purified. The polymer thus obtained exhibited Mn of 29,000, Mw of 45,000 and an acid value of 10 KOHmg/g.

Subsequently, 50 g of the polymer thus purified, 100 g of methylene chloride and 3 g of carbon black (Elftex 8, produced by Cablack Corp.) were kneaded in a ball mill for 24 hours. Methylene chloride lost during kneading was made up for. 31 g of the kneaded material was charged in a 200 ml three neck round flask equipped with an anchor agitator where it was then stirred to make a solution. The solution was then neutralized with 1.1 g of triethylamine (to a neutralization of 100%). To the reaction solution was then 1.2 g of 2-propanol. The agitation speed was raised to 450 rpm where 100 ml of distilled water was then added dropwise to the reaction solution in 30 minutes to cause phase inversion emulsification.

The reaction solution was then distilled at a temperature of 35° C. under reduced pressure for 1 hour to remove methylene chloride therefrom. The particles thus obtained were filtered off to obtain a wet cake. The wet cake thus obtained was washed with water, and then reverse-neutralized with diluted hydrochloric acid so that the neutralized salt structure present on the surface of the particles was converted to acid type. The material was washed with water, and then dried at a temperature of 40° C. under reduced pressure for 6 hours to obtain black microcapsuled particles having an average particle diameter of 12 µm. These microcapsuled particles were then observed under an optical microscope. As a result, a large number of carbon black particles were found present in the interior of particles having a smooth surface, demonstrating that the particles have a microcapsule structure. Even after dried, the particles underwent neither agglomeration nor blocking.

Example 4

Into a 200 ml separable three neck flask equipped with an agitator, a fractionating column and a nitrogen gas intake pipe were charged 96.0 g of L-lactide, 1.0 g of D-lactide, 3.0 g of the polyester (P1) obtained in Example 1, 0.5 g of ethylene glycol and 20 ml of toluene. In an atmosphere of nitrogen, the reaction components were melt-mixed at a temperature of 175° C. for 0.5 hour. To the reaction mixture was then added 0.03 g of tin octanoate. After 3 hours of reaction, the resulting polymer was sampled and measured for molecular weight Mn. The results were 16,000. To the polymer was then added 2.75 g of PMDA. The pressure in the reaction system was then reduced to 1 Pa at a temperature of 185° C. for 2 hours. The lactic acid-based polyester copolymer thus obtained exhibited Mn of 17,000, Mw of 20,000 and an acid value of 19 KOHmg/g.

Subsequently, into a 300 ml three neck round flask equipped with a turbine impeller mixer were charged 10 g of the polymer thus purified and 20.0 g of methylene chloride. These reaction components were stirred to make a solution. The solution thus obtained was then neutralized with 0.4 g of triethylamine (to a neutralization of 100%). The agitation speed was raised to 600 rpm where 200 ml of distilled water was then added dropwise to the reaction solution in 30 minutes to cause phase inversion emulsification. The reaction solution was then distilled at a temperature of 35° C. under reduced pressure for 1 hour to remove methylene chloride therefrom. The particles thus obtained were filtered off, washed with water, and then dried to obtain particles having an average particle diameter of 8 µm. Even after dried, the particles underwent neither agglomeration nor blocking.

Example 5

Into a 500 ml separable four neck flask equipped with an agitator, a fractionating column and a nitrogen gas intake pipe were charged 83.1 g of terephthalic acid, 83.1 g of isophthalic acid, 86.1 g of adipic acid and 121.0 g of ethylene glycol. In an atmosphere of nitrogen, the reaction components were melt-mixed at a temperature of 150° C. for 0.5 hour, and then stirred while being heated at a rate of 10° C./hr. The reaction mixture was heated to a temperature of 200° C. while water thus produced was being distilled off. After 6 hours, the termination of water distillation was confirmed. The pressure in the reaction system was then gradually reduced. When the pressure in the reaction system reached 20 Pa after 1 hour, the reaction product was then taken out. The aliphatic polyester thus obtained had a number-average molecular weight of 5,800 and a weight-average molecular weight of 11,000 (hereinafter simply referred to as "P4").

Into a 200 ml separable three neck flask equipped with an agitator, a fractionating column and a nitrogen gas intake pipe were charged 90.0 g of L-lactide, 10 g of the polymer (P4) and 20 ml of toluene. In an atmosphere of nitrogen, the reaction components were melt-mixed at a temperature of 175° C. for 0.5 hour. To the reaction mixture was then added 0.02 g of tin octanoate. After 3 hours of reaction, the resulting polymer was sampled and measured for molecular weight Mn. The results were 37,000. To the polymer was then added 0.81 g of adipic acid. The pressure in the reaction system was then reduced to 1 Pa at a temperature of 185° C. for 2 hours. The lactic acid-based polyester copolymer thus obtained exhibited Mn of 27,000, Mw of 53,000 and an acid value of 4 KOHmg/g.

Subsequently, into a 500 ml three neck round flask equipped with a turbine impeller mixer were charged 10 g of the polymer thus obtained and 100.0 g of tetrahydrofuran. These reaction components were stirred to make a solution. The solution thus obtained was then neutralized with 0.8 g of a 1 N aqueous solution of sodium hydroxide (to a neutralization of 100%).

The agitation speed was raised to 400 rpm where 200 ml of distilled water was then added dropwise to the reaction solution in 10 minutes to cause phase inversion emulsification. The reaction solution was then distilled at a temperature of 35° C. under reduced pressure for 1 hour to remove tetrahydrofuran therefrom. The particles thus obtained were filtered off, washed with water, and then dried to obtain particles having an average particle diameter of 221 Wm. Even after dried, the particles underwent neither agglomeration nor blocking.

Example 6

Into a 500 ml separable four neck flask equipped with an agitator, a fractionating column and a nitrogen gas intake pipe was charged 208.0 g of 90% L-lactic acid (produced by Purac Inc.). In an atmosphere of nitrogen, the reaction components were melt-mixed at a temperature of 150° C. for 0.5 hour, and then stirred while being heated at a rate of 20° C./hr. The reaction mixture was heated to a temperature of 190° C. while water thus produced was being distilled off. After 4 hours, the reduction of the pressure in the reaction system was allowed to begin. After 2 hours, the pressure in the reaction system reached 1 Pa where it was then kept for 2 hours. The polylactic acid thus obtained exhibited Mn of 5,200 and Mw of 8,400. 100 g of the polymer thus obtained and 4.30 g of PMDA were charged. The pressure in the reaction system was then reduced to 1 Pa for 2 hours. The polylactic acid thus obtained exhibited Mn of 4,100, Mw of 8,400 and an acid value of 32 KOHmg/g.

Subsequently, into a 500 ml three neck round flask equipped with a full-zone blade agitator were charged 10 g of the polymer thus obtained, 50.0 g of methylene chloride and 2.5 g of 2-propanol. These reaction components were stirred to make a solution. The solution thus obtained was then neutralized with 9.8 g of a 1 N aqueous solution of sodium hydroxide (to a neutralization of 100%). The agitation speed was raised to 400 rpm where 200 ml of distilled water was then added dropwise to the reaction solution in 3 minutes to cause phase inversion emulsification. The reaction solution was then distilled at a temperature of 35° C. under reduced pressure for 1 hour to remove methylene chloride therefrom. The particles thus obtained were filtered off, washed with water, and then dried at room temperature under reduced pressure to obtain particles having an average particle diameter of 0.2 µm. Even after dried, the particles underwent neither agglomeration nor blocking.

Example 7

Into a 200 ml separable three neck flask equipped with an agitator, a fractionating column and a nitrogen gas intake pipe was charged 100.0 g of L-lactide, 2.8 g of ethylene glycol and 20 ml of xylene. In an atmosphere of nitrogen, the reaction components were melt-mixed at a temperature of 195° C. for 0.5 hour. To the reaction mixture was then added 0.03 g of tin octanoate. After 3 hours of reaction, the resulting polymer was sampled and measured for molecular weight Mn and Mn. The results were Mn of 2,200 and Mw of 2,300. To the polymer was then added 10.0 g of pyromellitic anhydride. The reaction mixture was then allowed to undergo reaction at normal pressure and at 130° C. for 3 hours. The lactic acid-based polyester copolymer thus obtained exhibited Mn of 2,200, Mw of 2,500 and an acid value of 150 KOHmg/g.

Subsequently, into a 500 ml three neck round flask equipped with a paddle agitator were charged 10 g of the polymer thus obtained and 10.0 g of methylene chloride. These reaction components were stirred to make a solution. The solution thus obtained was then neutralized with 2.0 g of a 20 wt-% aqueous ammonia (to a neutralization of 20%). To the reaction solution was then added 1.0 g of 2-propanol. The agitation speed was raised to 500 rpm where 100 ml of distilled water was then added dropwise to the reaction solution in 10 minutes to cause phase inversion emulsification. The reaction solution was then distilled at a temperature of 35° C. under reduced pressure for 1 hour to remove methylene chloride therefrom. The particles thus obtained were filtered off, washed with water, and then dried to obtain particles having an average particle diameter of 0.09 Mm. Even after dried, the particles underwent neither agglomeration nor blocking.

Example 8

Into a 200 ml separable three neck flask equipped with an agitator, a fractionating column and a nitrogen gas intake pipe was charged 100.0 g of L-lactide, 3.0 g of dimethylolpropionic acid (hereinafter abbreviated as "DMPA) and 20 ml of toluene. In an atmosphere of nitrogen, the reaction components were melt-mixed at a temperature of 185° C. for 0.5 hour. To the reaction mixture was then added 0.03 g of titanium isopropoxide as a catalyst. After 3 hours of reaction, the resulting polymer was sampled and measured for molecular weight Mn and Mw. The results were Mn of 6,200 and Mw of 7,900. To the polymer was then added 3.6 g of succinic anhydride. The reaction mixture was then allowed to undergo reaction for 3 hours. The lactic acid-based polyester copolymer thus obtained exhibited Mn of 6,500, Mw of 8,100 and an acid value of 24 K()Hmg/g.

Subsequently, into a 500 ml three neck round flask equipped with a full-zone blade agitator were charged 10 g of the polymer thus obtained, 50.0 g of methyl ethyl ketone and 4.0 g of 2-propanol. These reaction components were stirred to make a solution. The solution thus obtained was then neutralized with 0.5 g of triethylamine (to a neutralization of 100%). The agitation speed was raised to 450 rpm where 100 ml of distilled water was then added dropwise to the reaction solution in 5 minutes to cause phase inversion emulsification. The reaction solution was then distilled at a temperature of 35° C. under reduced pressure for 1 hour to remove methyl ethyl ketone. The particles thus obtained were filtered off, washed with water, and then spray-dried to obtain particles having an average particle diameter of 1 µm. Even after dried, the particles underwent neither agglomeration nor blocking.

Example 9

Into a 200 ml separable three neck flask equipped with an agitator, a fractionating column and a nitrogen gas intake pipe was charged 70.0 g of L-lactide, 30.0 g of a copolymer of an ethylene oxide and a propylene oxide (Newpole PE-75, produced by SANYO CHEMICAL INDUSTRIES, LTD., Mn of 4, 000) and 20 ml of toluene. In an atmosphere of nitrogen, the reaction components were melt-mixed at a temperature of 175° C. for 0.5 hour. To the reaction mixture was then add ed 0.03 g of titanium isopropoxide as a catalyst.

After 2 hours of reaction, the resulting polymer was sampled and measured f or molecular weight Mn and Mn. The results were Mn of 16, 000 and Mw of 19, 000. To the polymer were then added 2.4 g of trimellitic anhydride and 0.05 g of pyridine. The reaction mixture was then allowed to undergo reaction for 3 hours. The lactic acid-based polyester copolymer thus obtained exhibited Mn of 15,000, Mw of 20,000 and an acid value of 14 KOHmg/g.

Subsequently, into a 500 ml three neck round flask equipped with a maxblend blade agitator were charged 10 g of the polymer thus obtained and 30.0 g of methylene chloride. These reaction components were stirred to make a solution. The solution thus obtained was then neutralized with 0.3 g of triethylamine (to a neutralization of 100%). The agitation speed was raised to 400 rpm where 200 ml of distilled water was then added dropwise to the reaction solution in 30 minutes to cause phase inversion emulsification. The reaction solution was then distilled at a temperature of 35° C. under reduced pressure for 1 hour to remove methylene chloride. The particles thus obtained were filtered off, washed with water, and then dried at a temperature of 40° C. under reduced pressure for 4 hours to obtain particles having an average particle diameter of 11 μm. Even after dried, the particles underwent neither agglomeration nor blocking.

Example 10

Into a 200 ml separable three neck flask equipped with an agitator, a fractionating column and a nitrogen gas intake pipe was charged 90.0 g of L-lactide, 10.0 g of a polyethylene glycol having Mn of 2,000 and 20 ml of toluene. In an atmosphere of nitrogen, the reaction components were melt-mixed at a temperature of 175° C. for 0.5 hour. To the reaction mixture was then added 0.03 g of tin octanoate as a catalyst. After 2 hours of reaction, the resulting polymer was sampled and measured for molecular weight Mn and Mn. The results were Mn of 18,000 and Mw of 20,000. To the polymer were then added 2.42 g of PMDA and 0.05 g of ferric acetylacetonate. The reaction mixture was then allowed to undergo reaction for 3 hours.

The lactic acid-based polyester copolymer thus obtained exhibited Mn of 16,000 and Mw of 20,000. The copolymer was dissolved in chloroform, and then reprecipitated with methanol so that it was purified. The polymer thus purified exhibited Mn of 17,000, Mw of 20,000 and an acid value of 18 KOHmg/g.

Subsequently, into a 500 ml three neck round flask equipped with a maxblend blade agitator were charged 10 g of the polymer thus obtained, 50.0 g of methyl ethyl ketone and 3 g of a phthalocyanine pigment (KET BLUE 104, produced by DAINIPPON INK & CHEMICALS, INC). These reaction components were stirred to make a dispersion. The dispersion thus obtained was then neutralized with 3.5 g of a 1 N aqueous solution of sodium hydroxide (to a neutralization of 100%). The agitation speed was raised to 300 rpm where 200 ml of distilled water was then added dropwise to the reaction solution in 1 minute to cause phase inversion emulsification.

The reaction solution was then distilled at a temperature of 35° C. under reduced pressure for 1 hour to remove methyl ethyl ketone therefrom. The particles thus obtained were filtered off, washed with water, and then dried at a temperature of 40° C. under reduced pressure for 4 hours to obtain blue microcapsuled particles having an average particle diameter of 7 μm. These microcapsuled particles were then observed under an optical microscope. As a result, a large number of blue pigment particles were found present in the interior of particles having a smooth surface, demonstrating that the particles have a microcapsule structure. Even after dried, the particles underwent neither agglomeration nor blocking.

Example 11

Into a 1 liter separable four neck flask equipped with an agitator, a fractionating column and a nitrogen gas intake pipe were charged 236.3 g of succinic acid and 234.3 g of 1,4-butylene glycol. In an atmosphere of nitrogen, the reaction components were melt-mixed at a temperature of 150° C. for 0.5 hour, and then stirred while being heated at a rate of 10° C./hr. The reaction mixture was heated to a temperature of 200° C. while water thus produced was being distilled off. After 6 hours, the termination of water distillation was confirmed. The pressure in the reaction system was then gradually reduced. When the pressure in the reaction system reached 20 Pa after 1 hour, the reaction was terminated.

The aliphatic polyester thus obtained (P5) exhibited Mn of 4,000and Mw of 7,200. 100 g of the polyester (P5) thus obtained, 10.9 g of tetrahydrocarboxylic anhydride of THF and 100 ml of toluene were charged into a 200 ml separable four neck flask equipped with an agitator, a fractionating column and a nitrogen gas intake pipe. These reaction components were melt-mixed at a temperature of 100° C. for 0.5 hour. To the reaction mixture was then added 0.05 g of ferric acetylacetonate. The reaction mixture was then allowed to undergo reaction for 2 hours. The aliphatic polyester thus obtained exhibited Mn of 4,100, Mw of 7,200 and an acid value of 62 KOHmg/g.

Subsequently, into a 500 ml three neck round flask equipped with a turbine impeller mixer were charged 10 g of the carboxylic acid-terminated polymer and 50.0 g of methyl ethyl ketone. These reaction components were stirred to make a solution. The solution thus obtained was then neutralized with 1.77 g of a 5 N aqueous solution of sodium hydroxide (to a neutralization of 80%). To the reaction solution was then added 3.0 g of 2-propanol. The agitation speed was raised to 400 rpm where 200 ml of distilled water was then added dropwise to the reaction solution in 30 minutes to cause phase inversion emulsification. The reaction solution was then distilled at a temperature of 35° C. under reduced pressure for 1 hour to remove methyl ethyl ketone therefrom. The particles thus obtained were filtered off, washed with water, and then dried to obtain particles having an average particle diameter of 0.05 Mm. Even after dried, the particles underwent neither agglomeration nor blocking.

Example 12

Into a 1 liter separable four neck flask equipped with an agitator, a fractionating column and a nitrogen gas intake pipe were charged 233.9 g of succinic acid, 109 g of trimellitic anhydride and 234.5 g of 1,4-butylene glycol. In an atmosphere of nitrogen, the reaction components were melt-mixed at a temperature of 150° C. for 0.5 hour, and then stirred while being heated at a rate of 10° C./hr. The reaction mixture was heated to a temperature of 200° C.

while water thus produced was being distilled off. After 6 hours, the termination of water distillation was confirmed. The pressure in the reaction system was then gradually reduced. When the pressure in the reaction system reached 20 Pa after 1 hour, the reaction was terminated.

The aliphatic polyester thus obtained exhibited Mn of 4,400 and Mw of 8,000. 100 g of the aliphatic polyester thus obtained and 7.0 g of succinic anhydride were charged into a 1 liter separable four neck flask equipped with an agitator, a fractionating column and a nitrogen gas intake pipe. These reaction components were then allowed to undergo reaction at a temperature of 200° C. under a pressure of 5 Pa for 0.5 hour. The aliphatic polyester thus obtained exhibited Mn of 5,100, Mw of 9,600 and an acid value of 30 KOHmg/g.

Subsequently, into a 500 ml three neck round flask equipped with a turbine impeller mixer were charged 10 g of the polymer comprising a carboxylic acid incorporated therein and 30.0 g of methylene chloride. These reaction components were stirred to make a solution. The solution thus obtained was then neutralized with 1.0 g of a 10% aqueous ammonia (to a neutralization of 100%) To the reaction solution was then added 3.0 g of 2-propanol. The agitation speed was raised to 500 rpm where 200 ml of distilled water was then added dropwise to the reaction solution in 30 minutes to cause phase inversion emulsification. The reaction solution was then distilled at a temperature of 35° C. under reduced pressure for 1 hour to remove methylene chloride therefrom. The particles thus obtained were filtered off, washed with water, and then dried to obtain particles having an average particle diameter of 0.8 $\mu$m. Even after dried, the particles underwent neither agglomeration nor blocking.

Example 13

Into a 1 liter separable four neck flask equipped with an agitator, a fractionating column and a nitrogen gas intake pipe were charged 236.3 g of succinic acid and 234.3 g of 1,4-butylene glycol. In an atmosphere of nitrogen, the reaction components were melt-mixed at a temperature of 150° C. for 0.5 hour, and then stirred while being heated at a rate of 10° C./hr. The reaction mixture was heated to a temperature of 200° C. while water thus produced was being distilled off. After 6 hours, the termination of water distillation was confirmed. To the reaction solution was then added 0.005 g of titanium isopropoxide. The pressure in the reaction system was then gradually reduced. When the pressure in the reaction system reached 0.1 Pa after 5 hours, the reaction was terminated.

The solid aliphatic polyester thus obtained exhibited Mn of 10,000 and Mw of 20,000. 100 g of the aliphatic polyester thus obtained, 4.4 g of PMDA and 0.03 g of imidazole were charged into a 1 liter separable four neck flask equipped with an agitator, a fractionating column and a nitrogen gas intake pipe. These reaction components were then allowed to undergo reaction at a temperature of 200° C. under a pressure of 1 Pa for 0.5 hour. The aliphatic polyester thus obtained exhibited Mn of 9,500, Mw of 22,000 and an acid value of 35 KOHmg/g.

Subsequently, into a 500 ml three neck round flask equipped with a turbine impeller mixer were charged 10 g of the polymer comprising a carboxylic acid incorporated therein and 20.0 g of methylene chloride. These reaction components were stirred to make a solution. The solution thus obtained was then neutralized with 0.7 g of triethylamine (to a neutralization of 100%). To the reaction solution was then added 3.0 g of 2-propanol. The agitation speed was raised to 450 rpm where 200 ml of distilled water was then added dropwise to the reaction solution in 5 minutes to cause phase inversion emulsification. The reaction solution was then distilled at a temperature of 35° C. under reduced pressure for 1 hour to remove methylene chloride therefrom. The particles thus obtained were filtered off, washed with water, and then dried under reduced pressure for 4 hours to obtain particles having an average particle diameter of 1 $\mu$m. Even after dried, the particles underwent neither agglomeration nor blocking.

Example 14

The procedure of phase inversion emulsification of Example 13 was followed except that the amount of triethylamine used was changed to 0.34 g and the percent neutralization was changed to 50%. As a result, particles having an average particle diameter of 14 $\mu$m were obtained.

Example 15

Into a 200 ml separable three neck flask equipped with an agitator, a fractionating column and a nitrogen gas intake pipe were charged 100.0 g of $\epsilon$-caprolactone, 1.5 g of ethylene glycol and 20 ml of toluene. In an atmosphere of nitrogen, the reaction components were then melt-mixed at a temperature of 160° C. for 0.5 hour. To the reaction solution was then added 0.05 g of stannous chloride as a catalyst. After 5 hours, the resulting polymer was sampled and measured for molecular weight Mn. The results were 7,200. To the reaction solution were then added 5.41 g of trimellitic anhydride and 0.05 g of pyridine. The reaction solution was then allowed to undergo reaction for 3 hours. The poly-$\epsilon$-caprolactone thus obtained exhibited Mn of 7,000, Mw of 8,300 and an acid value of 25 KOHmg/g.

Subsequently, into a 500 ml three neck round flask equipped with a turbine impeller mixer were charged 10 g of the poly-$\epsilon$-caprolactone comprising a carboxylic acid incorporated therein and 10.0 g of methylene chloride. These reaction components were stirred to make a solution. The solution thus obtained was then neutralized with 1.1 g of a 5 N aqueous solution of sodium hydroxide (to a neutralization of 100%). To the reaction solution was then added 3.0 g of 2-propanol. The agitation speed was raised to 300 rpm where 200 ml of distilled water was then added dropwise to the reaction solution in 60 minutes to cause phase inversion emulsification. The reaction solution was then distilled at a temperature of 25° C. under reduced pressure for 1 hour to remove methylene chloride therefrom. The particles thus obtained were filtered off, washed with water, and then dried at a temperature of 40° C. under reduced pressure to obtain particles having an average particle diameter of 3 $\mu$m. Even after dried, the particles underwent neither agglomeration nor blocking.

Example 16

Into a 200 ml separable three neck flask equipped with an agitator, a fractionating column and a nitrogen gas intake pipe were charged 100.0 g of $\epsilon$-caprolactone, 2.0 g of dimethylolpropionic acid and 20 ml of toluene. In an atmosphere of nitrogen, the reaction components were then melt-mixed at a temperature of 150° C. for 0.5 hour. To the reaction solution was then added 0.05 g of tin octanoate as a catalyst. After 2 hours of reaction, the resulting polymer was sampled and measured for molecular weight Mn and Mw. The results were Mn of 8,100 and Mw of 9,300. To the reaction solution were then added 5.53 g of PMDA and 0.05 g of a 1 N sulfuric acid. The reaction solution was then allowed to undergo reaction for 3 hours. The poly-ε-caprolactone thus obtained exhibited Mn of 8,500, Mw of 9,700 and an acid value of 35 KOHmg/g.

Subsequently, into a 500 ml three neck round flask equipped with a turbine impeller mixer were charged 10 g of the poly-ε-caprolactone comprising a carboxylic acid incorporated therein and 30.0 g of methylene chloride. These reaction components were stirred to make a solution. The solution thus obtained was then neutralized with 0.9 g of triethylamine (to a neutralization of 100%). The agitation speed was raised to 300 rpm where 100 ml of distilled water was then added dropwise to the reaction solution in 60 minutes to cause phase inversion emulsification. The reaction solution was then distilled at a temperature of 25° C. under reduced pressure for 1 hour to remove methylene chloride therefrom. The particles thus obtained were filtered off, washed with water, and then dried to obtain particles having an average particle diameter of 0.5 μm. Even after dried, the particles underwent neither agglomeration nor blocking.

Example 17

The procedure of phase inversion emulsification of Example 16 was followed except that the amount of triethylamine used was changed to 0.44 g and the percent neutralization was changed to 70%. As a result, particles having an average particle diameter of 4 μm were obtained.

Example 18

Into a 300 ml three neck round flask equipped with an anchor agitator were charged 10 g of the carboxylic acid-terminated resin obtained in Example 1, 10 g of Pyributycarb, 0.1 g of silica having an average particle diameter of 10 nm (SLM50650, produced by Hoechst Ltd.) and 50.0 g of methylene chloride. These reaction components were then stirred to make a solution. The solution thus obtained was then neutralized with 1.9 g of triethylamine (to a neutralization of 100%). To the reaction solution was then added 1.6 g of 2-propanol. The agitation speed was raised to 400 rpm where 200 ml of distilled water was then added dropwise to the reaction solution in 20 minutes to cause phase inversion emulsification.

Figure 3:
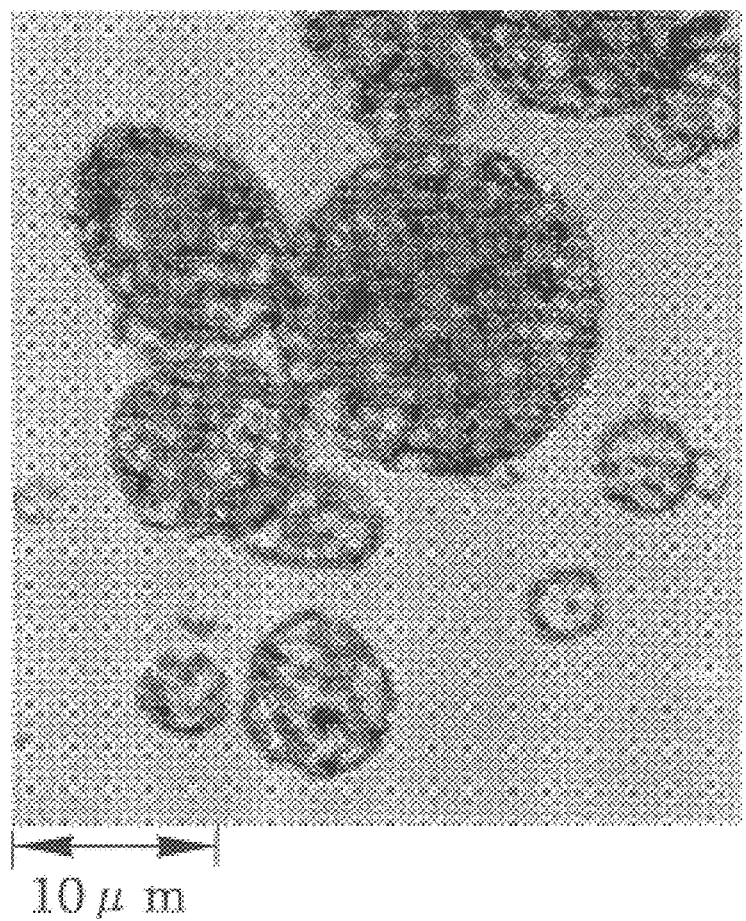
FIG. 3 is an optical microphotograph (magnification of ×1,250) of the self-water dispersible particle made of a biodegradable polyester containing a pesticide prepared in Example 18.

The reaction solution was then distilled at a temperature of 30° C. under reduced pressure for 1 hour to remove methylene chloride therefrom. Thus, an aqueous dispersion of capsuled pesticide having an average particle diameter of 20 μm was obtained. The particles thus obtained were filtered off, washed with water, and then dried at a temperature of 30° C. under reduced pressure. The particles underwent neither agglomeration nor blocking. An optical microphotograph of the capsuled pesticide thus obtained is shown in FIG. 3 at a magnification of ×1,250.

Example 19

Into a 300 ml three neck round flask equipped with an anchor agitator were charged 10 g of the carboxylic acid-terminated resin obtained in Example 2, 8 g of Pyributycarb, 0.2 g of silica having an average particle diameter of 10 nm (SLM50650, produced by Hoechst Ltd.) and 10 g of methyl ethyl ketone. These reaction components were then stirred to make a solution. The solution thus obtained was then neutralized with 2.6 g of a 0.1 N aqueous solution of sodium hydroxide (to a neutralization of 100%). To the reaction solution was then added 2.5 g of 2-propanol.

The agitation speed was raised to 500 rpm where 200 ml of distilled water was then added dropwise to the reaction solution in 30 minutes to cause phase inversion emulsification. The reaction solution was then distilled at a temperature of 35° C. under reduced pressure for 1 hour to remove methyl ethyl ketone therefrom. Thus, an aqueous dispersion of capsuled pesticide having an average particle diameter of 8 μm was obtained. The particles thus obtained were filtered off, washed with water, and then dried at a temperature of 30° C. under reduced pressure for 4 hours. The particles underwent neither agglomeration nor blocking.

Example 20

Into a 500 ml three neck round flask equipped with a full-zone blade agitator were charged 10 g of the carboxylic acid-terminated resin obtained in Example 6, 5 g of Pyributycarb, 0.08 g of calcium carbonate having an average particle diameter of 20 nm, 50.0 g of methylene chloride and 2.5 g of 2-propanol. These reaction components were then stirred to make a solution. The solution thus obtained was then neutralized with 9.8 g of a 1 N aqueous solution of sodium hydroxide (to a neutralization of 100%).

The agitation speed was raised to 400 rpm where 200 ml of distilled water was then added dropwise to the reaction solution in 3 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 0.5 μm was obtained. The particles thus obtained were filtered off, washed with water, and then dried at a temperature of 30° C. under reduced pressure for 4 hours. The particles underwent neither agglomeration nor blocking.

Example 21

Into a 500 ml three neck round flask equipped with a paddle agitator were charged 10 g of the carboxylic acid-terminated resin obtained in Example 7, 2 g of Pyributycarb, 0.05 g of calcium carbonate having an average particle diameter of 20 nm and 10.0 g of methylene chloride. These reaction components were then stirred to make a solution. The solution thus obtained was then neutralized with 2.0 g of a 20 wt-% aqueous ammonia (to a neutralization of 20%). To the reaction solution was then added 1.0 g of 2-propanol.

The agitation speed was raised to 500 rpm where 100 ml of distilled water was then added dropwise to the reaction solution in 10 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 0.15 μm was obtained. The particles thus obtained were filtered off, washed with water, and then dried at a temperature of 30° C. under reduced pressure for 4 hours. The particles underwent neither agglomeration nor blocking.

Example 22

Into a 500 ml three neck round flask equipped with a full-zone blade agitator were charged 10 g of the carboxylic acid-terminated resin obtained in Example 8, 2 g of Pyributycarb, 0.1 g of titanium oxide having an average particle diameter of 15 nm (MT-150W, produced by TAYCA CORP.), 50.0 g of methyl ethyl ketone and 4.0 g of 2-propanol. These reaction components were then stirred to make a solution. The solution thus obtained was then neutralized with 0.5 g of triethylamine (to a neutralization of 100%). The agitation speed was raised to 450 rpm where 100 ml of distilled water was then added dropwise to the reaction solution in 5 minutes to cause phase inversion emulsification. The reaction solution was then distilled at a temperature of 35° C. under reduced pressure for 1 hour to remove methyl ethyl ketone therefrom. Thus, an aqueous dispersion of capsuled pesticide having an average particle diameter of 1.4 μm was obtained. The particles thus obtained were filtered off, washed with water, and then dried at a temperature of 30° C. under reduced pressure for 4 hours. The particles underwent neither agglomeration nor blocking.

Example 23

Into a 500 ml three neck round flask equipped with a maxblend blade agitator were charged 10 g of the carboxylic acid-terminated resin obtained in Example 9, 10 g of Pyributycarb and 30.0 g of methylene chloride. These reaction components were then stirred to make a solution. The solution thus obtained was then neutralized with 0.3 g of triethylamine (to a neutralization of 100%). The agitation speed was raised to 400 rpm where 200 ml of distilled water was then added dropwise to the reaction solution in 30 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 13 μm was obtained. The particles thus obtained were filtered off, washed with water, and then dried at a temperature of 30° C. under reduced pressure for 4 hours. The particles underwent neither agglomeration nor blocking.

Example 24

Into a 500 ml three neck round flask equipped with a turbine impeller mixer were charged 10 g of the carboxylic acid-terminated resin obtained in Example 11, 10 g of Pyributycarb and 50.0 g of methyl ethyl ketone. These reaction components were then stirred to make a solution. The solution thus obtained was then neutralized with 1.77 g of a 5 N aqueous solution of sodium hydroxide (to a neutralization of 80%). To the reaction solution was then added 3.0 g of 2-propanol. The agitation speed was raised to 400 rpm where 200 ml of distilled water was then added dropwise to the reaction solution in 30 minutes to cause phase inversion emulsification. The reaction solution was then distilled at a temperature of 35° C. under reduced pressure for 1 hour to remove methyl ethyl ketone therefrom. Thus, an aqueous dispersion of capsuled pesticide having an average particle diameter of 0.09 μm was obtained. The particles thus obtained were filtered off, washed with water, and then dried at a temperature of 30° C. under reduced pressure for 4 hours. The particles underwent neither agglomeration nor blocking.

Example 25

Into a 500 ml three neck round flask equipped with a turbine impeller mixer were charged 10 g of the carboxylic acid-terminated polymer obtained in Example 12, 5 g of Pyributycarb and 30.0 g of methylene chloride. These reaction components were then stirred to make a solution. The solution thus obtained was then neutralized with 1.0 g of a 10% aqueous ammonia (to a neutralization of 100%). To the reaction solution was then added 3.0 g of 2-propanol. The agitation speed was raised to 500 rpm where 200 ml of distilled water was then added dropwise to the reaction solution in 30 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 1.1 μm was obtained. The particles thus obtained were filtered off, washed with water, and then dried at a temperature of 30° C. under reduced pressure for 4 hours. The particles underwent neither agglomeration nor blocking.

Example 26

Into a 500 ml three neck round flask equipped with a turbine impeller mixer were charged 10 g of the carboxylic acid-terminated polymer obtained in Example 14, 5 g of Pyributycarb, 0.08 g of silica having an average particle diameter of 10 nm (SLM50650, produced by Hoechst Ltd.) and 20.0 g of methylene chloride. These reaction components were then stirred to make a solution. The solution thus obtained was then neutralized with 0.34 g of triethylamine (to a neutralization of 50%). To the reaction solution was then added 3.0 g of 2-propanol. The agitation speed was raised to 450 rpm where 200 ml of distilled water was then added dropwise to the reaction solution in 5 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 1.9 μm was obtained. The particles thus obtained were filtered off, washed with water, and then dried at a temperature of 30° C. under reduced pressure for 4 hours. The particles underwent neither agglomeration nor blocking.

Example 27

Into a 500 ml three neck round flask equipped with a turbine impeller mixer were charged 10 g of the carboxylic acid-terminated polymer obtained in Example 17, 8 g of Pyributycarb, 0.15 g of titanium oxide having an average particle diameter of 15 nm (MT-150W, produced TAYCA CORP.) and 30.0 g of methylene chloride. These reaction components were then stirred to make a solution. The solution thus obtained was then neutralized with 0.44 g of triethylamine (to a neutralization of 50%). The agitation speed was raised to 300 rpm where 100 ml of distilled water was then added dropwise to the reaction solution in 60 minutes to cause phase inversion emulsification. The reaction solution was then distilled at a temperature of 25° C. under reduced pressure for 1 hour to remove methylene chloride therefrom. Thus, an aqueous dispersion of capsuled pesticide having an average particle diameter of 7.2 μm was obtained. The particles thus obtained were filtered off, washed with water, and then dried at a temperature of 30° C. under reduced pressure for 4 hours. The particles underwent neither agglomeration nor blocking.

Example 28

Into a 300 ml three neck round flask equipped with an anchor agitator were charged 10 g of the carboxylic acid-terminated resin obtained in Example 1, 10 g of Bellkute, 0.1 g of silica having an average particle diameter of 10 nm (SLM50650, produced by Hoechst Ltd.) and 40.0 g of methylene chloride. These reaction components were then stirred to make a solution. The solution thus obtained was then neutralized with 1.9 g of triethylamine (to a neutralization of 100%). To the reaction solution was then added 1.6 g of 2-propanol. The agitation speed was raised to 500 rpm where 300 ml of distilled water was then added dropwise to the reaction solution in 30 minutes to cause phase inversion emulsification. The reaction solution was then distilled at a temperature of 30° C. under reduced pressure for 1 hour to remove methylene chloride therefrom. Thus, an aqueous dispersion of capsuled pesticide having an average particle diameter of 22 μm was obtained. The particles thus obtained were filtered off, washed with water, and then dried under reduced pressure by a freeze dryer for 24 hours. The particles underwent neither agglomeration nor blocking. Thus, a capsulized agent was obtained in powder form.

Example 29

Into a 300 ml three neck round flask equipped with an anchor agitator were charged 10 g of the carboxylic acid-terminated resin obtained in Example 2, 8 g of Bellkute, 0.2 g of silica having an average particle diameter of 10 nm (SLM50650, produced by Hoechst Ltd.) and 10 g of methyl ethyl ketone. These reaction components were then stirred to make a solution. The solution thus obtained was then neutralized with 2.6 g of a 0.1 N aqueous solution of sodium hydroxide (to a neutralization of 100%). To the reaction solution was then added 2.5 g of 2-propanol.

The agitation speed was raised to 1,200 rpm where 200 ml of distilled water was then added dropwise to the reaction solution in 30 minutes to cause phase inversion emulsification. The reaction solution was then distilled at a temperature of 35° C. under reduced pressure for 1 hour to remove methyl ethyl ketone therefrom. Thus, an aqueous dispersion of capsuled pesticide having an average particle diameter of 8 μm was obtained. The particles thus obtained were filtered off, washed with water, and then dried under reduced pressure by a freeze dryer for 48 hours. The particles underwent neither agglomeration nor blocking. Thus, a capsulized agent was obtained in powder form.

Example 30

Into a 500 ml three neck round flask equipped with a full-zone blade agitator were charged 10 g of the carboxylic acid-terminated resin obtained in Example 6, 5 g of Bellkute, 0.08 g of calcium carbonate having an average particle diameter of 18 nm, 45.0 g of methylene chloride and 2.5 g of 2-propanol. These reaction components were then stirred to make a solution. The solution thus obtained was then neutralized with 9.8 g of a 1 N aqueous solution of sodium hydroxide (to a neutralization of 100%). The agitation speed was raised to 300 rpm where 200 ml of distilled water was then added dropwise to the reaction solution in 10 minutes to cause phase inversion emulsification. The reaction solution was then distilled at a temperature of 35° C. under reduced pressure for 1 hour to remove methylene chloride therefrom. Thus, an aqueous dispersion of capsuled pesticide having an average particle diameter of 0.7 μm was obtained. The particles thus obtained were filtered off, washed with water, and then dried at a temperature of 20° C. under reduced pressure for 12 hours. The particles underwent neither agglomeration nor blocking. Thus, a capsulized agent was obtained in powder form.

Example 31

Into a 500 ml three neck round flask equipped with a paddle agitator were charged 10 g of the carboxylic acid-terminated resin obtained in Example 7, 2 g of Bellkute, 0.05 g of calcium carbonate having an average particle diameter of 20 nm and 10.0 g of methylene chloride. These reaction components were then stirred to make a solution. The solution thus obtained was then neutralized with 2.0 g of a 20 wt-% aqueous ammonia (to a neutralization of 20%). To the reaction solution was then added 1.0 g of 2-propanol.

The agitation speed was raised to 500 rpm where 100 ml of distilled water was then added dropwise to the reaction solution in 20 minutes to cause phase inversion emulsification. The reaction solution was then distilled at a temperature of 30° C. under reduced pressure for 1 hour to remove methylene chloride therefrom. Thus, an aqueous dispersion of capsuled pesticide having an average particle diameter of 0.13 μm was obtained. The particles thus obtained were filtered off, washed with water, and then dried under reduced pressure by a freeze dryer for 48 hours. The particles underwent neither agglomeration nor blocking. Thus, a capsulized agent was obtained in powder form.

Example 32

Into a 500 ml three neck round flask equipped with a full-zone blade agitator were charged 10 g of the carboxylic acid-terminated resin obtained in Example 8, 2 g of Dithiopyr, 0.1 g of titanium oxide having an average particle diameter of 15 nm (MT-150W, produced TAYCA CORP.), 35.0 g of methyl ethyl ketone and 3.0 g of 2-propanol. These reaction components were then stirred to make a solution. The solution thus obtained was then neutralized with 0.5 g of triethylamine (to a neutralization of 100%). The agitation speed was raised to 1,200 rpm where 100 ml of distilled water was then added dropwise to the reaction solution in 5 minutes to cause phase inversion emulsification. The reaction solution was then distilled at a temperature of 35° C. under reduced pressure for 1 hour to remove methyl ethyl ketone therefrom. Thus, an aqueous dispersion of capsuled pesticide having an average particle diameter of 1.1 μm was obtained. The particles thus obtained were filtered off, washed with water, and then dried under reduced pressure by a freeze dryer for 48 hours. The particles underwent neither agglomeration nor blocking. Thus, a capsulized agent was obtained in powder form.

Comparative Example 1

Into a 500 ml three neck round flask equipped with a turbine impeller mixer were charged 10 g of the polyester (P2), 30.0 g of methylene chloride and 3.0 g of 2-propanol. These reaction components were stirred to make a solution. The agitation speed was raised to 300 rpm where 200 ml of distilled water was then added dropwise to the reaction solution in 30 minutes. However, the reaction solution didn't undergo phase inversion emulsification, causing the precipitation of the polymer.

Comparative Example 2

Into a 500 ml three neck round flask equipped with a turbine impeller mixer were charged 10 g of the polyester (P5), 30.0 g of methylene chloride and 3.0 g of 2-propanol. These reaction components were stirred to make a solution. The agitation speed was raised to 300 rpm where 200 ml of distilled water was then added dropwise to the reaction solution in 30 minutes. However, the reaction solution didn't undergo phase inversion emulsification, causing the precipitation of the polymer.

The results of the self-water dispersible polyesters obtained in the foregoing examples are set forth in Tables 1 to 6. The abbreviations set forth in the tables below have the following meanings: LD: Lactide; LA: Lactic acid; ε-CL: ε-Caprolactone; EG: Ethylene glycol; BG: 1,4-Butylene glycol; AA: Adipic acid; SeA: Sebasic acid; SuA: Succinic acid; SuAn: Succinic anhydride; TPA: Terephthalic acid; IPA: Isophthalic acid; PMDA: Pyromellitic anhydride; TMAn: Trimellitic anhydride; TAn: Tetracarboxylic anhydride of THF; DMPA: Dimethylolpropionic acid

TABLE 1

| Example No. | 1 | 2 | 3 | 4 | 5 | 6 |
|---|---|---|---|---|---|---|
| Starting material 1 | P1 | P2 | P3 | P1 | LA | LA |
| Starting material 2 | LD | LD | LD | LD | — | — |
| Starting material 3 | EG | — | — | — | — | — |
| Polymer as starting material (Mn × $10^{-3}$) | 6.2 | 7.0 | 31 | 16 | 27 | 5.2 |
| Acid group-introducing agent | PMDA | PMDA | PMDA | PMDA | AA | PMDA |
| Molecular weight of polymer having acid groups incorporated therein (Mn × $10^{-3}$) | 16 | 9.2 | 29 | 17 | 28 | 4.1 |
| Acid value (KOH mg/g) | 14 | 21 | 10 | 19 | 4 | 32 |
| Neutralizing agent | TEA | NaOH | TEA | TEA | NaOH | NaOH |
| % Neutralization | 100 | 100 | 100 | 100 | 100 | 100 |
| Neutralized acid value (KOH mg/g) | 14 | 21 | 10 | 19 | 4 | 32 |
| Average particle diameter (μm) | 20 | 5 | 12 | 8 | 221 | 0.2 |

TABLE 2

| Example No. | 7 | 8 | 9 | 10 | 11 | 12 |
|---|---|---|---|---|---|---|
| Starting material 1 | LD | LD | PE75 | PEG | SuA | SuA |
| Starting material 2 | EG | DMPA | LD | LD | BG | TMAn |
| Starting material 3 | — | — | — | — | — | BG |
| Polymer as starting material (Mn × $10^{-3}$) | 2.2 | 6.2 | 16 | 18 | 4.0 | 4.4 |
| Acid group-introducing agent | SuAn | SuAn | TMAn | PMDA | TAn | SuAn |
| Molecular weight of polymer having acid groups incorporated therein (Mn × $10^{-3}$) | 2.2 | 6.5 | 15 | 16 | 4.1 | 5.1 |
| Acid value (KOH mg/g) | 150 | 24 | 14 | 18 | 62 | 30 |
| Neutralizing agent | $NH_3$ | TEA | TEA | NaOH | NaOH | $NH_3$ |
| % Neutralization | 20 | 100 | 100 | 100 | 80 | 100 |
| Neutralized acid value (KOH mg/g) | 30 | 24 | 14 | 18 | 49.6 | 30 |
| Average particle diameter (μm) | 0.09 | 1 | 1 | 7 | 0.05 | 0.8 |

TABLE 3

| Example No. | 13 | 14 | 15 | 16 | 17 |
|---|---|---|---|---|---|
| Starting material 1 | SuA | SuA | ε-CL | ε-CL | ε-CL |
| Starting material 2 | BG | BG | EG | DMPA | DMPA |
| Starting material 3 | — | — | — | — | — |
| Polymer as starting material (Mn × $10^{-3}$) | 10 | 10 | 7.2 | 8.1 | 8.1 |
| Acid group-introducing agent | PMDA | PMDA | PMDA | PMDA | PMDA |
| Molecular weight of polymer having acid groups incorporated therein (Mn × $10^{-3}$) | 9.5 | 9.5 | 7.0 | 7.8 | 7.8 |
| Acid value (KOH mg/g) | 28 | 28 | 25 | 35 | 35 |
| Neutralizing agent | TEA | TEA | NaOH | TEA | TEA |
| % Neutralization | 100 | 50 | 100 | 100 | 70 |
| Neutralized acid value (KOH mg/g) | 28 | 14 | 25 | 35 | 24.5 |
| Average particle diameter (μm) | 1 | 14 | 3 | 0.5 | 4 |

TABLE 4

| Example No. | 18 | 19 | 20 | 21 | 22 |
|---|---|---|---|---|---|
| Starting material resin 1 | P1 | P2 | LA | LD | LD |
| Starting material resin 2 | LD | LD | — | EG | DMPA |
| Starting material resin 3 | EG | — | — | — | — |
| Molecular weight of resin having acid groups incorporated therein (Mn × $10^{-3}$) | 16 | 9.2 | 4.1 | 2.2 | 6.5 |
| Amount of resin (g) | 10 | 10 | 10 | 10 | 10 |
| Pesticide | | | Pyributycarb | | |
| Amount of pesticide (g) | 10 | 8 | 5 | 2 | 2 |
| Inorganic material | Silica | Silica | Calcium carbonate | Calcium carbonate | Titanium oxide |
| Amount of inorganic material (g) | 0.1 | 0.2 | 0.08 | 0.05 | 0.1 |

TABLE 4-continued

| Example No. | 18 | 19 | 20 | 21 | 22 |
|---|---|---|---|---|---|
| Neutralizing agent | TEA | NaOH | NaOH | $NH_3$ | TEA |
| % Neutralization | 100 | 100 | 100 | 20 | 100 |
| Neutralized acid value (KOH mg/g) | 14 | 21 | 32 | 30 | 24 |
| Particle diameter of capsulized pesticide ($\mu$m) | 20 | 8 | 0.5 | 0.15 | 1.4 |

TABLE 5

| Example No. | 23 | 24 | 25 | 26 | 27 |
|---|---|---|---|---|---|
| Starting material resin 1 | PE75 | SuA | SuA | SuA | $\epsilon$-CL |
| Starting material resin 2 | LD | BG | TMAn | BG | DMPA |
| Starting material resin 3 | — | — | BG | — | — |
| Molecular weight of resin having acid groups incorporated therein ($Mn \times 10^{-3}$) | 15 | 4.1 | 5.1 | 9.5 | 7.8 |
| Amount of resin (g) | 10 | 10 | 10 | 10 | 10 |
| Pesticide | | | Pyributycarb | | |
| Amount of pesticide (g) | 10 | 10 | 5 | 5 | 8 |
| Inorganic material | — | — | — | Silica | Titanium oxide |
| Amount of inorganic material (g) | — | — | — | 0.08 | 0.15 |
| Neutralizing agent | TEA | NaOH | $NH_3$ | TEA | TEA |
| % Neutralization | 100 | 80 | 100 | 50 | 70 |
| Neutralized acid value (KOH mg/g) | 14 | 49.6 | 30 | 14 | 24.5 |
| Particle diameter of capsulized pesticide ($\mu$m) | 13 | 0.09 | 1.1 | 1.9 | 7.2 |

TABLE 6

| Example No. | 28 | 29 | 30 | 31 | 32 |
|---|---|---|---|---|---|
| Starting material resin 1 | P1 | P2 | LA | LD | LD |
| Starting material resin 2 | LD | LD | — | EG | DMPA |
| Starting material resin 3 | EG | — | — | — | — |
| Molecular weight of resin having acid groups incorporated therein ($Mn \times 10^{-3}$) | 16 | 9.2 | 4.1 | 2.2 | 6.5 |
| Amount of resin (g) | 10 | 10 | 10 | 10 | 10 |
| Pesticide | | | Bellkute | | Dithiopyr |
| Amount of pesticide (g) | 10 | 8 | 5 | 2 | 2 |
| Inorganic material | Silica | Silica | Calcium carbonate | Calcium carbonate | Titanium oxide |
| Amount of inorganic material (g) | 0.1 | 0.2 | 0.08 | 0.05 | 0.1 |
| Neutralizing agent | TEA | NaOH | NaOH | $NH_3$ | TEA |
| % Neutralization | 100 | 100 | 100 | 20 | 100 |
| Neutralized acid value (KOH mg/g) | 14 | 21 | 32 | 30 | 24 |
| Particle diameter of capsulized pesticide ($\mu$m) | 22 | 8 | 0.7 | 0.13 | 1.1 |

Comparative Example 3 (Preparation of Hydrated Pyributycarb)

To 12 g of Pyributycarb were added 1 g of a polyoxyethylene tristyryl phenyl ether (SOPROPHOR BSU, produced by Rhone Poulenc Japan Ltd.), 3 g of a polyoxyethylene styryl phenyl ether sulfate (SORPOL 7556, produced by Toho Chemical Industries, Ltd.), 1.5 g of a hydrophobic silica (REOLOSIL MT-10C, produced by Tokuyama Co., Ltd.), 5 g of propylene glycol and 77.5 g of water. The mixture was then subjected to dispersion by a homogenizer to obtain a hydrated Pyributycarb (effective content of Pyributycarb: 12% by weight).

Subsequently, the capsulized pesticides of Examples 18 to 27 and the hydrated Pyributycarb of Comparative Example 3 were examined for residual effect to evaluate their gradual releasability.

Evaluating Test for Residual Effect

A 1/5,000a Wagner pot was filled with gravel, puddled paddy soil and puddled and levelled paddy soil (alluvial soil) in this order from the bottom thereof. The pot was then flooded to a height of about 4 cm. The various chemicals were each dispersed in water, and then added dropwise to the pot through a Pasteur pipette. From the following day, water was sprayed onto the pot at a rate of 2 cm/day for 2 days. Thereafter, the pot was kept flooded to a height of 1 cm. When a predetermined number of days passed, *Echinochloa*

*oryzicola* seeds which had been forcedly sprouted were planted in the soil in the pot at a depth of 5 mm at an angle of 45° using a forceps.

These seeds thus planted were then allowed to grow for 2 weeks. The plants were then sampled at the surface of the soil, and then measured for weight. The percent inhibition was then calculated by the following equation.

% Inhibition=100−(Weight of pesticide-treated zone/Weight of untreated zone×100)

This test was repeated twice for each of the pesticides. These measurements were then averaged. For the criterion of judgement of medical effect, when the percent inhibition was not less than 50%, the medical effect was judged fair.

For comparison, a pot sprayed with 11 mg of hydrated Pyributycarb (Pyributycarb content: 1.3 mg) and an untreated pot were examined. The amount of the various capsuled pesticides to be sprayed for evaluating test for residual effect was predetermined such that the content of Pyributycarb was 1.3 mg. The results are set forth in Table 7 and FIG. 1. All these capsuled pesticides exhibited an excellent gradual releasability, i.e., excellent retention of medical effect as compared with the uncapsuled hydrated Pyributycarb of Comparative Example 3.

TABLE 7

| Evaluating test for residual effect | % Inhibition of *Echinochloa oryzicola* Elapsed time (week) after treatment of capsuled pesticide | | | | | | |
|---|---|---|---|---|---|---|---|
| | 3 | 4 | 5 | 6 | 7 | 8 | 9 |
| 18 | 100 | 100 | 100 | 100 | 85 | 25 | 25 |
| 19 | 100 | 100 | 100 | 100 | 90 | 50 | 20 |
| 20 | 100 | 100 | 100 | 90 | 50 | 0 | 0 |
| 21 | 100 | 100 | 100 | 80 | 70 | 30 | 0 |
| 22 | 100 | 100 | 100 | 100 | 75 | 50 | 40 |
| 23 | 100 | 100 | 100 | 100 | 60 | 50 | 40 |
| 24 | 100 | 100 | 100 | 100 | 80 | 50 | 0 |
| 25 | 100 | 100 | 100 | 100 | 75 | 25 | 25 |
| 26 | 100 | 100 | 100 | 100 | 50 | 20 | 0 |
| 27 | 100 | 100 | 100 | 75 | 50 | 25 | 20 |
| Pyributycarb | 100 | 100 | 100 | 25 | 10 | 0 | 0 |
| Untreated | 0 | 0 | 0 | 0 | 0 | 0 | 0 |

The present invention can provide a self-water dispersible particle made of a biodegradable polyester having varied average particle diameters of the order of nanometer free of urethane bond and excellent in biodegradability, an aqueous dispersion thereof, a self-water dispersible particle made of a biodegradable polyester comprising a hydrophobic core material encapsulated therein excellent in gradual releasability such as pesticide, and a process for the simple preparation of these products without using any auxiliary stabilizing material such as emulsifying agent or any high speed agitator.

What is claimed is:

1. A self-water dispersible particle made of a biodegradable polyester.

2. The self-water dispersible particle made of a biodegradable polyester according to claim 1, wherein said biodegradable polyester contains carboxyl groups and/or salt thereof.

3. The self-water dispersible particle made of a biodegradable polyester according to claim 2, wherein said biodegradable polyester has an acid value of from 4 to 200 KOHmg/g.

4. The self-water dispersible particle made of a biodegradable polyester according to claim 3, wherein said biodegradable polyester contains dimethylolpropionic acid residues.

5. The self-water dispersible particle made of a biodegradable polyester according to any one of claims 1 to 4, wherein said biodegradable polyester is a lactic acid-based polymer.

6. The self-water dispersible particle made of a biodegradable polyester according to any one of claims 1 to 4, wherein said biodegradable polyester is an aliphatic polyester.

7. The self-water dispersible particle made of a biodegradable polyester according to any one of claims 1 to 4, wherein said biodegradable polyester is a lactone-based polymer.

8. The self-water dispersible particle made of a biodegradable polyester according to claim 5, wherein said lactic acid-based polymer is a polylactic acid.

9. The self-water dispersible particle made of a biodegradable polyester according to claim 5, wherein said lactic acid-based polymer is a lactic acid-based polyester copolymer comprising a lactic acid unit and a polyester unit.

10. The self-water dispersible particle made of a biodegradable polyester according to any one of claims 1 to 4, comprising a hydrophobic core material encapsulated therein.

11. The self-water dispersible particle made of a biodegradable polyester according to claim 10, wherein said hydrophobic core material is an effective component of pesticide.

\* \* \* \* \*